(12) United States Patent
Lee et al.

(10) Patent No.: US 10,273,506 B2
(45) Date of Patent: Apr. 30, 2019

(54) HOST CELLS AND METHODS FOR PRODUCING ISOPENTENOL FROM MEVALONATE

(71) Applicant: The Regents of the University of California, Oakland, CA (US)

(72) Inventors: Taek Soon Lee, Berkeley, CA (US); Aram Kang, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/682,325

(22) Filed: Aug. 21, 2017

(65) Prior Publication Data

US 2018/0080052 A1 Mar. 22, 2018

Related U.S. Application Data

(63) Continuation of application No. PCT/US2016/018984, filed on Feb. 22, 2016.

(60) Provisional application No. 62/119,071, filed on Feb. 20, 2015.

(51) Int. Cl.
| | |
|---|---|
| *C12N 1/20* | (2006.01) |
| *C12P 7/04* | (2006.01) |
| *C07F 9/09* | (2006.01) |
| *C08F 136/08* | (2006.01) |
| *C12P 5/00* | (2006.01) |
| *C12N 9/16* | (2006.01) |
| *C12N 9/88* | (2006.01) |
| *C12N 9/04* | (2006.01) |
| *C12N 9/10* | (2006.01) |
| *C12N 9/12* | (2006.01) |

(52) U.S. Cl.
CPC .............. *C12P 7/04* (2013.01); *C07F 9/091* (2013.01); *C07F 9/098* (2013.01); *C08F 136/08* (2013.01); *C12N 9/0006* (2013.01); *C12N 9/1025* (2013.01); *C12N 9/1205* (2013.01); *C12N 9/16* (2013.01); *C12N 9/88* (2013.01); *C12P 5/007* (2013.01); *C12Y 101/01088* (2013.01); *C12Y 203/0301* (2013.01); *C12Y 207/01036* (2013.01); *C12Y 401/01033* (2013.01)

(58) Field of Classification Search
CPC .......... C12P 5/007; C12N 9/1229; C12N 9/88
USPC ........................ 435/52, 119, 127, 232, 252.3
See application file for complete search history.

(56) References Cited

U.S. PATENT DOCUMENTS

2013/0089906 A1   4/2013   Beck et al.

FOREIGN PATENT DOCUMENTS

| WO | 2014/100726 A2 | 6/2014 |
| WO | WO2014/100726 A2 * | 6/2014 |

OTHER PUBLICATIONS

Patent Cooperation Treaty, PCT/US2016/018984 dated Feb. 6, 2016, "PCT Notification of Transmittal of the International Search Report and the Written Opinion of the International Searching Authority, or the Declaration." ISA, including Forms PCT/ISA/220, 210, and Form 237 (2016).
George et al., "Metabolic engineering for the high-yield production of isoprenoid-based C5 alcohols in *E. coli*," Scientific Reports, vol. 5, No. 11128, pp. 1-12 (2015).
Kang et al., "Isopentenyldiphosphate (IPP)—bypass mevalonate pathways for isopentenol production," Metabolic Engineering, vol. 34, pp. 25-35 (2015).
Kang et al., "Converting sugars to Biofuels: Ethanol and Beyond," Bioengineering, vol. 2, pp. 184-203 (2015).
Anthony et al., "Optimization of the mevalonate-based isoprenoid biosynthetic pathway in *Escherichia coli* for production of the anti-malarial drug precursor annorpha-4,11-diene." Metab. Eng., vol. 11, pp. 13-19 (2009).
Adolfsen et al., "Futile cycling increases sensitivity toward oxidative stress in *Escherichia coli*." Metab. Eng., vol. 29, pp. 26-35 (2015).
Alonso-Gutierrez et al., "Metabolic engineering of *Escherichia coli* for limonene and perillyl alcohol production." Metab Eng., vol. 19, pp. 33-41 (2013).
Barta et al., "Structural basis for nucleotide binding and reaction catalysis in mevalonate diphosphate decarboxylase." Biochemistry, vol. 51, pp. 5611-5621.
Baba et al., "Construction of *Escherichia coli* K-12 in-frame, single-gene knockout mutants: the Keio collection." Mol. Syst. Biol., vol. 2, pp. 2006-0008 (2006).
Bonanno et al., "Structural genomics of enzymes involved in sterol/isoprenoidbiosynthesis." Proc. Natl. Acad. Sci. USA., vol. 98, pp. 12896-12901 (2001).
Chou et al., "Synthetic pathway for production of five-carbon alcohols from isopentenyl diphosphate." Appl. Environ. Microbiol., vol. 78, pp. 7849-7855 (2012).

(Continued)

*Primary Examiner* — Tekchand Saidha
(74) *Attorney, Agent, or Firm* — Robin C. Chang; Lawrence Berkeley National Laboratory

(57) ABSTRACT

The present invention provides for a genetically modified host cell capable of producing isopentenol and/or 3-methyl-3-butenol, comprising (a) an increased expression of phosphomevalonate decarboxylase (PMD) (b) an increased expression of a phosphatase capable of converting isopentenol into 3-methyl-3-butenol, (c) optionally the genetically modified host cell does not express, or has a decreased expression of one or more of NudB, phosphomevalonate kinase (PMK), and/or PMD, and (d) optionally one or more further enzymes capable of converting isopentenol and/or 3-methyl-3-butenol into a third compound, such as isoprene.

17 Claims, 27 Drawing Sheets

Specification includes a Sequence Listing.

(56) References Cited

OTHER PUBLICATIONS

Connor et al., "Engineering of an *Escherichia coli* strain for the production of 3-methyl-1-butanol." Appl. Environ. Microbiol., vol. 74, pp. 5769-5775 (2008).
Connor et al., "3-Methyl-1-butanol production in *Escherichia coli*: Random mutagenesis and two-phase fermentation." Appl. Microbiol. Biotechnol., vol. 86, pp. 1155-1164 (2010).
Cohen, "Functional linkage between genes that regulate osmotic stress responses and multidrug resistance transporters: challenges and opportunities for antibiotic discovery." Antimicrob. Agents Chemother., vol. 58, pp. 640-646 (2014).
Clark et al., "Biochemical Engineering." Second Edition CRC Press, book accessed online Dec. 8, 2015 (1997). https://books.google.com/books?id=ST_p2AOApZsC&lpg=PR3&ots=zYn6G-1z5o&lr&pg=PR1#v=onepage&q&f=false.
Dueber et al., "Synthetic protein scaffolds provide modular control over metabolic flux." Nat. Biotechnol., vol. 27, pp. 753-759 (2009).
Dahl et al., "Engineering dynamic pathway regulation using stress-response promoters." Nat. Biotechnol., vol. 31, pp. 1039-1046 (2013).
Degenhardt et al., "Monoterpene and sesquiterpene synthases and the origin of terpene skeletal diversity in plants." Phytochemistry. vol. 70, pp. 1621-1637 (2009).
George et al., "Correlation analysis of targeted proteins and metabolites to assess and engineer microbial isopentenol production." Biotechnol. Bioeng., vol. 111, pp. 1648-1658 (2014).
George et al., "Metabolic engineering for the high-yield production of isoprenoid-based C5 alcohols in *E. coli*.," Sci. Rep., vol. 5, pp. 11128 (2015).
Gogerty et al., "Formation of isobutene from 3-hydroxy-3-methylbutyrate by diphosphomevalonate decarboxylase." Appl. Environ. Microbiol., vol. 76, pp. 8004-8010 (2010).
Hengge, "The two-component network and the general stress sigma factor RpoS (sigmaS) in *Escherichia coli*." Adv. Exp. Med. Biol., vol. 631, pp. 40-53 (2008).
Kim et al., "Microbial Synthesis of Myrcene by Metabolically Engineered *Escherichia coli*." J. Agric. Food Chem., vol. 63, pp. 4606-4612 (2015).
Krepkiy et al., "Identification of active site residues in mevalonate diphosphate decarboxylase: implications for a family of phosphotransferases." Protein Sci., vol. 13, pp. 1875-1881 (2004).
Liu et al., "Combination of entner-doudoroff pathway with MEP increases isoprene production in engineered *Escherichia coli*." PLoS One, vol. 8, e83290 (2013).
Lee et al., "BglBrick vectors and datasheets: a synthetic biology platform for gene expression." J. Biol. Eng., vol. 5, pp. 12 (2011).
Martin et al., "Engineering a mevalonate pathway in *Escherichia coli* for production of terpenoids." Nat. Biotechnol., vol. 21, pp. 796-802 (2003).
Ma et al., "Optimization of a heterologous mevalonate pathway through the use of variant HMG-CoA reductases." Metab. Eng., vol. 13, pp. 588-597 (2011).
Peralta-Yahya et al., "Microbial engineering for the production of advanced biofuels." Nature., vol. 488, pp. 320-328 (2012).
Pfleger et al., "Combinatorial engineering of intergenic regions in operons tunes expression of multiple genes." Nat. Biotechnol., vol. 24, pp. 1027-1032 (2006).
Pitera et al., "Balancing a heterologous mevalonate pathway for improved isoprenoid production in *Escherichia coli*." Metab. Eng., vol. 9, pp. 193-207 (2007).
Redding-Johanson et al., "Targeted proteomics for metabolic pathway optimization: Application to terpene production." Metab. Eng., vol. 13, pp. 194-203 (2011).
Sun et al., "ATP requirement for acidic resistance in *Escherichia coli*." J. Bacteriol., vol. 193, pp. 3072-3077 (2011).
Vannice et al., "Identification in Haloferax volcanii of phosphomevalonate decarboxylase and isopentenyl phosphate kinase as catalysts of the terminal enzyme reactions in an archaeal alternate mevalonate pathway." J. Bacteriol., vol. 196, pp. 1055-1063.
Withers et al., "Identification of isopentenol biosynthetic genes from Bacillus subtilis by a screening method based on isoprenoid precursor toxicity." Appl. Environ. Microbiol., vol. 73, pp. 6277-6283 (2007).
Wang et al., "Farnesol production from *Escherichia coli* by harnessing the exogenous mevalonate pathway." Biotechnol. Bioeng., vol. 107, pp. 421-429 (2010).
Wagner et al., "Tuning *Escherichia coli* for membrane protein overexpression." Proc. Natl. Acad. Sci. USA., vol. 105, pp. 14371-14376 (2008).
Zheng et al., "Metabolic engineering of *Escherichia coli* for high-specificity production of isoprenol and prenol as next generation of biofuels." Biotechnol. Biofuels, vol. 6, p. 57 (2013).
Zhu et al., "In vitro reconstitution of mevalonate pathway and targeted engineering of farnesene overproduction in *Escherichia coli*." Biotechnol. Bioeng., vol. 111, pp. 1396-1405 (2014).

\* cited by examiner

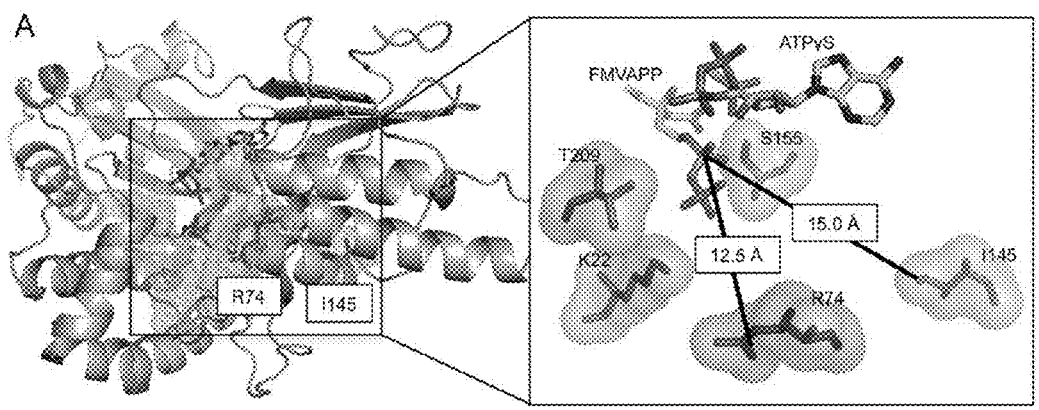
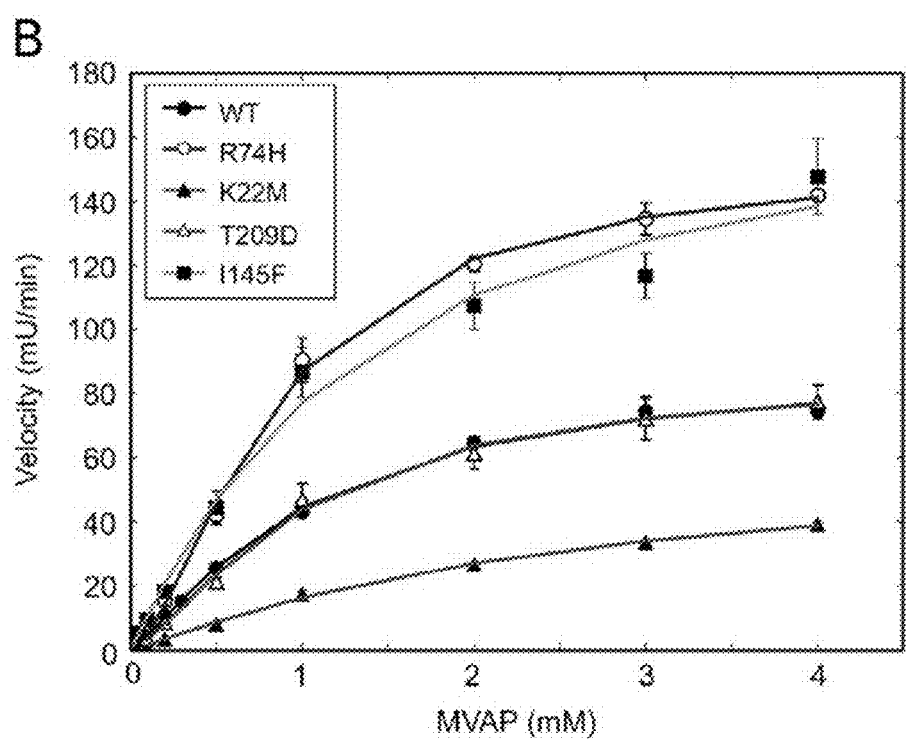
Figure 17A
Figure 17B

Figure 21

SEQUENCE LISTING

```
<160> NUMBER OF SEQ ID NOS: 2

<210> SEQ ID NO 1
<211> LENGTH: 396
<212> TYPE: PRT
<213> ORGANISM: Saccharomyces cerevisiae

<400> SEQUENCE: 1

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320
```

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395

<210> SEQ ID NO 2
<211> LENGTH: 327
<212> TYPE: PRT
<213> ORGANISM: Staphylococcus epidermidis

<400> SEQUENCE: 2

Met Val Lys Ser Gly Lys Ala Arg Ala His Thr Asn Ile Ala Leu Ile
1               5                   10                  15

Lys Tyr Trp Gly Lys Ala Asp Glu Thr Tyr Ile Ile Pro Met Asn Asn
            20                  25                  30

Ser Leu Ser Val Thr Leu Asp Arg Phe Tyr Thr Glu Thr Lys Val Thr
        35                  40                  45

Phe Asp Pro Asp Phe Thr Glu Asp Cys Leu Ile Leu Asn Gly Asn Glu
    50                  55                  60

Val Asn Ala Lys Glu Lys Glu Lys Ile Gln Asn Tyr Met Asn Ile Val
65                  70                  75                  80

Arg Asp Leu Ala Gly Asn Arg Leu His Ala Arg Ile Glu Ser Glu Asn
                85                  90                  95

Tyr Val Pro Thr Ala Ala Gly Leu Ala Ser Ser Ala Ser Ala Tyr Ala
            100                 105                 110

Ala Leu Ala Ala Ala Cys Asn Glu Ala Leu Ser Leu Asn Leu Ser Asp
        115                 120                 125

Thr Asp Leu Ser Arg Leu Ala Arg Arg Gly Ser Gly Ser Ala Ser Arg
    130                 135                 140

Ser Ile Phe Gly Gly Phe Ala Glu Trp Glu Lys Gly His Asp Asp Leu
145                 150                 155                 160

Thr Ser Tyr Ala His Gly Ile Asn Ser Asn Gly Trp Glu Lys Asp Leu
                165                 170                 175

Ser Met Ile Phe Val Val Ile Asn Asn Gln Ser Lys Lys Val Ser Ser
            180                 185                 190

Arg Ser Gly Met Ser Leu Thr Arg Asp Thr Ser Arg Phe Tyr Gln Tyr
        195                 200                 205

Trp Leu Asp His Val Asp Glu Asp Leu Asn Glu Ala Lys Glu Ala Val
    210                 215                 220

Lys Asn Gln Asp Phe Gln Arg Leu Gly Glu Val Ile Glu Ala Asn Gly
225                 230                 235                 240

Leu Arg Met His Ala Thr Asn Leu Gly Ala Gln Pro Pro Phe Thr Tyr
                245                 250                 255

Leu Val Gln Glu Ser Tyr Asp Ala Met Ala Ile Val Glu Gln Cys Arg
            260                 265                 270

Lys Ala Asn Leu Pro Cys Tyr Phe Thr Met Asp Ala Gly Pro Asn Val
        275                 280                 285

Lys Val Leu Val Glu Lys Lys Asn Lys Gln Ala Val Met Glu Gln Phe

```
            290                 295                 300
Leu Lys Val Phe Asp Glu Ser Lys Ile Ile Ala Ser Asp Ile Ile Ser
305                 310                 315                 320

Ser Gly Val Glu Ile Ile Lys
                325
```

HOST CELLS AND METHODS FOR PRODUCING ISOPENTENOL FROM MEVALONATE

RELATED PATENT APPLICATIONS

The application claims priority as a continuation application to PCT International Patent Application No. PCT/US16/18984, filed Feb. 22, 2016, which claims priority to U.S. Provisional Patent Application Ser. No. 62/119,071, filed Feb. 20, 2015; both of which are incorporated herein by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of producing isopentenol.

BACKGROUND OF THE INVENTION

The mevalonate pathway has been extensively used to produce a range of valuable chemicals via isopentenyl pyrophosphates (IPP) or dimethylallyl pyrophosphates (DMAPP) as essential intermediates for terpene synthesis. In addition to terpene-based chemicals, Chou and colleagues engineered the mevalonate pathway in Escherichia coli to produce isopentenols via hydrolysis of IPP to 3-methyl-3-butenol (Chou and Keasling, Appl. Environ. Microbiol. 2012). In this pathway, 3 ATPs are required to produce one molecule of IPP from one molecule of mevalonate. Among these 3 ATPs, two ATPs are consumed for two-step phosphorylations to produce mevalonate pyrophosphate, but the pyrophosphate group is subsequently hydrolyzed to produce isopentenol from IPP. As a result, the overall pathway is not only energetically demanding but also inefficient because of unnecessary phosphorylation-dephosphorylation steps. Furthermore, the energy and cost demand of this pathway has been a problem, especially when a production in large scale using fermentor is exploited since it requires extensive aeration to facilitate ATP generation in E. coli.

To our knowledge, there has been no report that attempts to resolve the aforementioned problem in the mevalonate-derived isopentenol pathway. Although there were other pathways reported to produce isopentenols of which carbon backbones were derived from keto acids intermediates in biosynthesis pathways of valine, leucine and isoleucine (Atsumi et al. Nature 2008). However, biosynthesis of these amino acids from pyruvate requires multiple biochemical reactions, which are tightly regulated in E. coli. In addition, to produce isopentenols from these keto acids precursors, two more enzymes (keto acids decarboxylase and alcohol dehydrogenase) are required. Given of E. coli strains and pathways that produce mevalonate in a high titer, we hope to invent a new pathway that lower down the energy cost per isopentenol synthesis from mevalonate by bypassing the phosphorylation reactions performed by mevalonate kinase (MK) and phosphomevalonate kinase (PMK) towards a more cost-effective biological system.

SUMMARY OF THE INVENTION

The present invention provides for a genetically modified host cell capable of producing isopentenol and/or 3-methyl-3-butenol, comprising (a) an increased expression of phosphomevalonate decarboxylase (PMD) (b) an increased expression of a phosphatase capable of converting isopentenol into 3-methyl-3-butenol, (c) optionally the genetically modified host cell does not express, or has a decreased expression of one or more of NudB, PMK, and/or PMD, and (d) optionally one or more further enzymes capable of converting isopentenol and/or 3-methyl-3-butenol into a third compound, such as isoprene. In some embodiments, the decreased expression is a disruption of the promoter or knock out of the gene encoding the enzyme.

In some embodiments, the genetically modified host cell further comprises an increased expression of one or more of AtoB, hydroxymethylglutaryl-CoA synthase (HMGS), hydroxymethylglutaryl-CoA reductase (HMGR), and/or MK.

In some embodiments, one or more of the described expressed enzymes, such as PMD, phosphatase, AtoB, HMGS, HMGR, and/or MK, are encoded on one or more nucleotide sequences which are in one or more nucleic acids which are transformed into the genetically modified host cell, or host cell prior to genetic modification. In some embodiments, the nucleotide sequences encoding the one or more enzymes are operatively linked to one or more promoters capable of transcription in the genetically modified host cell. In some embodiments, each nucleic acid of the one or more nucleic acids is a vector capable of stable introduction into and/or maintenance in the host cell.

The present invention provides for a method for producing isopentenol and/or 3-methyl-3-butenol and/or the third compound, comprising: (a) providing a genetically modified host cell of the present invention, (b) culturing the genetically modified host cell under a condition wherein PMD and/or phosphatase are expressed, and (c) optionally recovering the isopentenol and/or 3-methyl-3-butenol and/or the third compound.

In some embodiments, the (b) culturing step further comprises expressing AtoB, HMGS, HMGR, and/or MK. In some embodiments, the (b) culturing step is under an anaerobic or microaerobic condition.

In some embodiments, one or more of the enzymes, including PMD, phosphatase, AtoB, HMGS, HMGR, and MK, is an engineered enzyme, or homologous, mutant or variant enzymes having the same enzymatic activity, with an amino acid sequence having equal to or more than 70%, 80%, 90%, 95%, or 99% identity to the amino acid sequence of the corresponding wild-type enzyme, such as the specific enzymes described in Examples 1, 2, or 3.

In some embodiments, one or more of the enzymes, including PMD, phosphatase, AtoB, HMGS, HMGR, and MK, is heterologous to the host cell.

In some embodiments, the genetically modified host cell is capable of producing one or more compounds in titers or yields equal to or more than the titers or yields described herein.

The present invention provides for a mutant or engineered enzyme described in Examples 1, 2, or 3, including, but not limited to, a PMD mutants described in Example 3. The present invention provides for PMD mutants comprising an amino acid sequence substantially identically to the amino acid sequence of a wild type PMD, such as PMDsc or PMDse, wherein the PMD mutant comprises one or more of the amino acid mutations described in Example 3.

BRIEF DESCRIPTION OF THE DRAWINGS

The foregoing aspects and others will be readily appreciated by the skilled artisan from the following description of illustrative embodiments when read in conjunction with the accompanying drawings.

FIG. 17A. Effect of mutations on isopentenol production with IPP-bypass pathway II. Location of R74 and I145 in $PMD_{sc}$. Blue meshes are essential residues for catalysis and substrate binding, and pink meshes are residues selected for mutagenesis. Electrostatic interactions are not clearly found between substrates and these residues and the distance between phosphate group of the substrate analog (6-fluoromevalonate 5-diphosphate (FMVAPP)) and R74 or I145 residue are 12.5 Å or 15.0 Å, respectively.

FIG. 17B. Effect of mutations on isopentenol production with IPP-bypass pathway II. Curve fittings and kinetics of $PMD_{sc}$ wild type and four mutants (K22M, R74H, I145F and T209D).

FIG. 21. Amino acid sequence comparison between *Saccharomyces cerevisiae* PMD (Seq_1, SEQ ID NO:1) and *S. epidermis* PMD (Seq_2, SEQ ID NO:2).

DETAILED DESCRIPTION OF THE INVENTION

Figure 1:
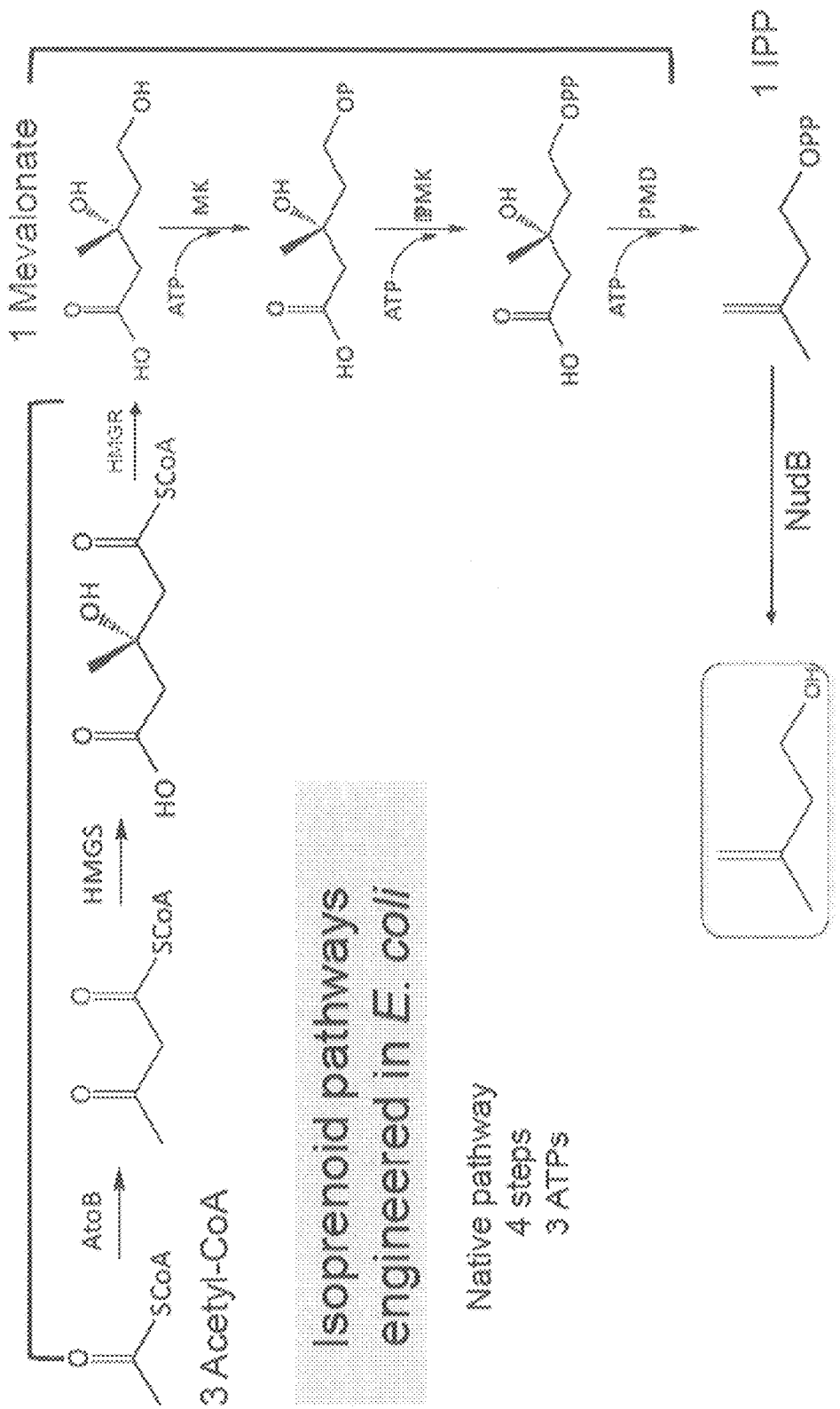
FIG. 1. Mevalonate pathway for isopentenol production from acetyl CoA. The original pathway needs two step phosphorylation of mevalonate for isopentenyl diphosphate (IPP) production by mevalonate kinase (MK) and phosphomevalonate kinase (PMK) before decarboxylative elimination by phosphomevalonate decarboxylase (PMD).

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "enzyme" includes a single enzyme as well as a plurality of enzymes, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous" as used herein refers to a composition, such as enzyme or nucleic acid, or the like, that in nature is not found together with another composition. For example, an enzyme is heterologous to a host cell, if in nature the species of the host cell does not have the enzyme.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "substantially identical" describes an amino acid sequence that is at least 70%, 75%, 80%, 85%, 90%, 95% or 99% identical to any one of the amino acid sequence described herein. The "substantially identical" amino acid sequence may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity, as compared to the enzyme described herein. The "substantially identical" enzyme has an enzymatic activity that is identical or essentially identical to the biological activity of the regulator or enzyme described herein. The "substantially identical" enzyme may be found in nature, i.e. naturally occurring, or be an engineered mutant thereof.

Figure 21:
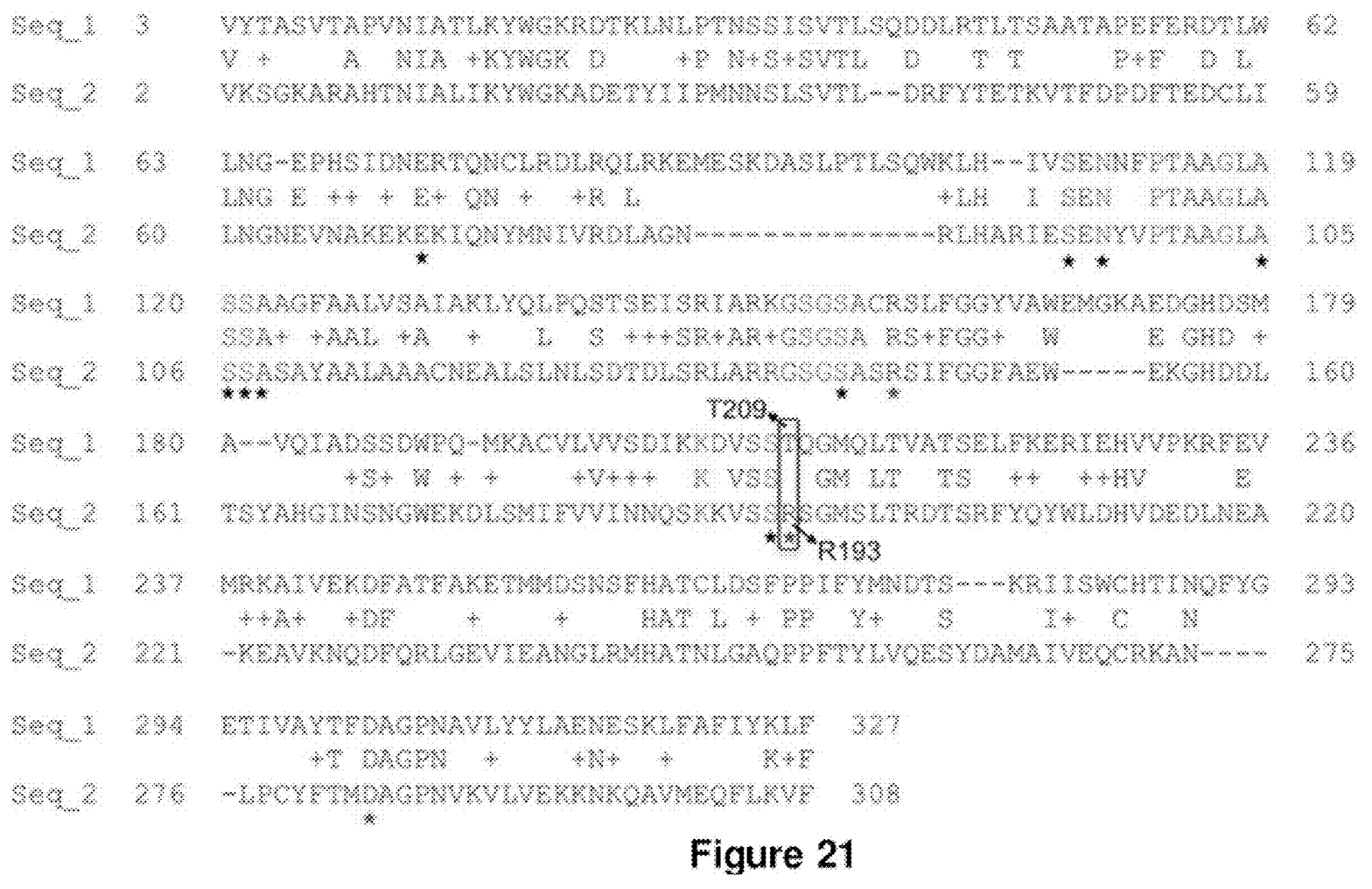

The PMD is any suitable PMD, such as any PMD with an amino acid sequence substantially identical to the amino acid sequences of SEQ ID NO: 1 or 2. The substantially identical PMD comprises one or more, or all, of the conserved residues are identified in FIG. 21, including but not limited to one or more, or all, of the conserved residues indicated by a star.

The host cell can be a eukaryote or prokaryote cell that produces acetyl-CoA. Any prokaryotic or eukaryotic host cell may be used in the present method so long as it remains viable after being transformed with a sequence of nucleic acids. Generally, although not necessarily, the host cell is bacterial. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla, Paracoccus*, and Clostridia taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, fungal, insect or mammalian cells. Suitable fungal cells are yeast cells, such as yeast cells of the *Saccharomyces* genus.

One of the advantages of the present invention is the improvement in cost-effectiveness of isopentenol production in a host cell, such as *E. coli*, under condition, such as oxygen-limited conditions of industrial scale—whether aerobic or anaerobic.

Prior approaches to making isopentenol/chemicals via IPP (isopentenyl pyrophosphate) consume three ATPs between mevalonate and IPP. These prior approaches contain unnecessary phosphorylation-dephosphorylation steps which consume energy, are inefficient, and require expensive aeration in large tanks. For example, see FIG. 1.

In some embodiments, the host cells comprise pathways which go directly or via two-steps from mevalonate to isopentenol. For example, see FIGS. 2 and 3. Reduced energy requirements mean less aeration is required, alleviating ATP as a limiting factor in aerobic and anaerobic applications of mevalonate pathway.

The present invention provides one or more of the following advantages. (1) Improved yields (carbon and redox balances of the modified pathways are basically same as the original pathway). The method has an improved efficiency and reduced costs at the industrial scale by reduced or eliminated need for aeration during the culturing of the host cells. (2) IPP toxicity is relieved: IPP toxicity is a key factor in limiting pathway function in the original isopentenol pathway (George et al. Biotech Bioeng 2014). Modified pathways do not generate IPP. (3) Higher isopentenol production. In an experiment, a host cell with the pathway in FIG. 2 produced ~900 mg/L of isopentenol after 42 hrs incubation, which is about 40% higher than a titer obtained from a host cell with the original pathway (FIG. 1) under aerobic condition (640 mg/L). (4) Apparent better growth: Cells with the modified pathway show better growth giving final OD above 3.5 under aerobic conditions, versus ~2.7 for *E. coli* strains with the original pathway. Under anaerobic conditions, some host cells with the modified pathway have been shown to have a better growth (28% higher OD). (5) Potentially less leakage: The decreased number of enzymes in modified pathways decreases level of protein synthesis, and improves efficiency by decreasing possible loss to intermediates. Removing IPP biosynthesis minimizes cross-talk with other native *coli* metabolism.

In some embodiments, the host cell is capable of carrying out the following steps: biological hydrogenation of isopentenol to isopentanol via IP→DMAP→3-methyl-2-buteno-1→isopentanol by engineered IDI and NemA.

In some embodiments, the host cell is further capable of carrying out the following step: isopentenol→isoprene.

To decrease energy cost for production of isopentenol, we have invented two novel biosynthesis pathways that implement engineered phosphomevalonate decarboxylase (PMD). In the original pathway, PMD catalyzes the reaction that converts diphosphomevalonate to isopentenyl diphosphate, which is subsequently hydrolyzed to 3-methyl-3-butenol. However, in our first new pathways, the engineered PMD enabled *E. coli* to bypass two phosphorylation steps to produce 3-methyl-3-butenol directly from mevalonate. On the other hand, in the second new pathway, PMD removes carboxylate group from mevalonate phosphate and produce isopentenyl phosphate (IP). Subsequently, the second pathway introduces the engineered IP phosphatase to produce isopentenol. These new pathways have advantages over the existing isopentenol pathway: first, the new pathways diminish ATP demand by one or two while the existing pathway requires three ATP molecules per one molecule of 3-methyl-3-butenol, which makes the new pathway more energetically efficient. Second, the new pathways decrease the number of enzymes by two (PMK, NudB) or three (MK, PMK, NudB) than that of the existing pathway. The decreased number of enzymes in the new pathways not only decreases the cost for protein synthesis but also allows intermediates to be more efficiently fluxed to isopentenol by decreasing possible loss of intermediates. In the existing isopentenol pathway, mevalonate is not a native substrate in *E. coli*, but IPP is utilized and lost by native enzymes in *E. coli*. However, the new pathways bypass IPP biosynthesis, which removes toxicity of IPP, and minimize crosstalk between the isopentenol pathway and the native metabolisms. The developed new pathways will be further improved for oxygen-limited conditions by optimizing cofactors for redox balance (e.g. NADH) of top portion enzymes that catalyze the transformation from acetyl-CoA to mevalonate. In summary, the new isopentenol pathways invented here improve cost-effectiveness of the overall pathways in *E. coli* under oxygen-limited conditions towards industrial scale-up.

First of all, the modified pathways in this invention do not improve theoretical maximum yield for isopentenol since the carbon and redox balances of the modified pathways are basically same as the original pathway.

The advantages of this pathway are one or more of the following: (1) This pathway would be more favored than the original pathway not only in the aerobic but also in the anaerobic fermentation condition, since it requires less ATP which is one of the limiting factors both in aerobic and anaerobic application of mevalonate pathway. (2) Aeration is also one of the most expensive processes in industrial application, and relieving (not removing but relieving) the requirement of aeration would have a huge benefit for industrial application. (3) We can also relieve the IPP toxicity issue of the original pathway using these modified pathways. In the original pathway for isopentenol, the pathway balance has been a very important issue and IPP toxicity is one of the key factors to limit the pathway function (George et al. Biotech Bioeng 2014). One of the modified pathways of the present invention overcomes this toxicity issue since it does not generate toxic IPP from the modified pathway which in turn makes large scale/high flux production of isopentenol possible.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

A Modified MVA Pathway for Isopentenol Production

Isoprenoids are considered as one of the most promising advanced biofuels. Among the isoprenoid compounds, branched C5 alcohols (3-methyl-butanol, 3-methyl-3-butenol, and 3-methyl-2-butenol) have been tested as good biofuel compounds with favorable combustion properties and octane numbers to gasoline. A synthetic pathway for C5 alcohols production has been reported previously in *E. coli* using the heterologous mevalonate (MVA) pathway, and further metabolic engineering efforts on this synthetic pathway have led to over 50% theoretical yield in the C5 alcohol production.

Even though the MVA pathway has been known to be less efficient than the MEP pathway in carbon and redox balance as well as in energy balance, the MVA pathway has been extensively used for microbial production of a range of valuable isoprenoids due to its tractability and the high titers it can provide. However, the energy demands of this pathway and the operational cost for aeration to meet the energy demands have been a problem when a production in large scale using fermentor is exploited. Presented herein are modified pathways for C5 alcohol production that will address these issues of the traditional MVA pathways.

The mevalonate pathway condenses 3 molecules of acetyl-CoA to produce one molecule of isopentenyl pyrophosphate (IPP). One of the intermediate, mevalonate is phosphorylated twice by two different kinases, mevalonate kinase (MK) and phosphomevalonate kinase (PMK), and lastly diphosphomevalonate decarboxylase removes the carboxylate group resulting in isopentenol pyrophosphate.

This study aims to identify and engineer an enzyme that catalyzes the decarboxylation of phosphomevalonate or mevalonate to isopentenyl monophosphate or isopentenol. One initially seeks a decarboxylation activity from diphosphomevalonate decarboxylase from *Saccharomyces cerevisiae*, and confirms the activity by in vitro enzyme assay. Searching for a better decarboxylase enzyme, various diphosphomevalonate decarboxylases from other two species, *Staphylococcus epidermis* and *Haloferax volacanii*, have been tested, but the decarboxylase of the mevalonate pathway in *S. cerevisiae* results in the highest titer of isopentenol in vivo in the bypass pathway that produces isopentenol via isopentenyl monophosphate and mevalonate monophosphate. The investigation of the decarboxylase activity for mevalonate is not limited to the diphosphomevalonate decarboxylases family in the mevalonate pathways, and engineering of promiscuous activity of the decarboxylase for mevalonate can be extended to other enzyme families such as fatty acid decarboxylases.

In vitro assay shows that hydrolysis of isopentenyl monophosphate can be a limiting step if decarboxylation step is not the rate-limiting reaction. To identify the endogenous phosphatase, which hydrolyze the isopentenyl monophosphate producing isopentenol, 36 endogenous monophosphatase mutants of *E. coli* have been screened. Initial screening shows that three mutants produced less isopentenol compared to that of the wild type, and over-expression of one of the three phosphatase genes resulted in much faster conversion of isopentenyl monophosphate to isopentenol compared to other two phosphatase genes.

Figure 2:
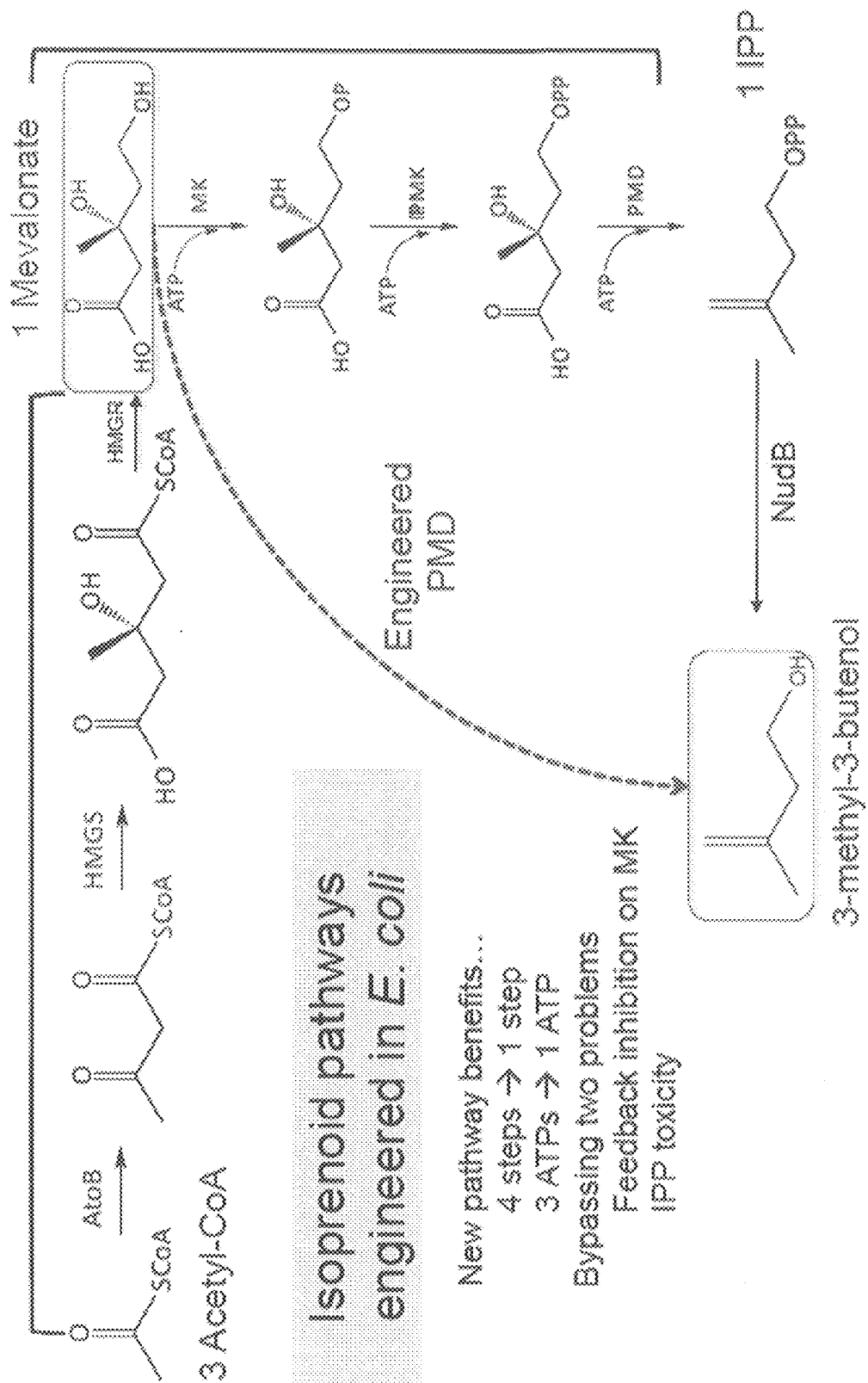
FIG. 2. The first modified pathway for isopentenol from acetyl CoA. Mevalonate is directly converted to isopentenol through decarboxylative elimination by PMD (or engineered PMD). This modified pathway is a single step conversion from mevalonate to isopentenol and saves 2 ATPs from the original pathway.
Figure 3:
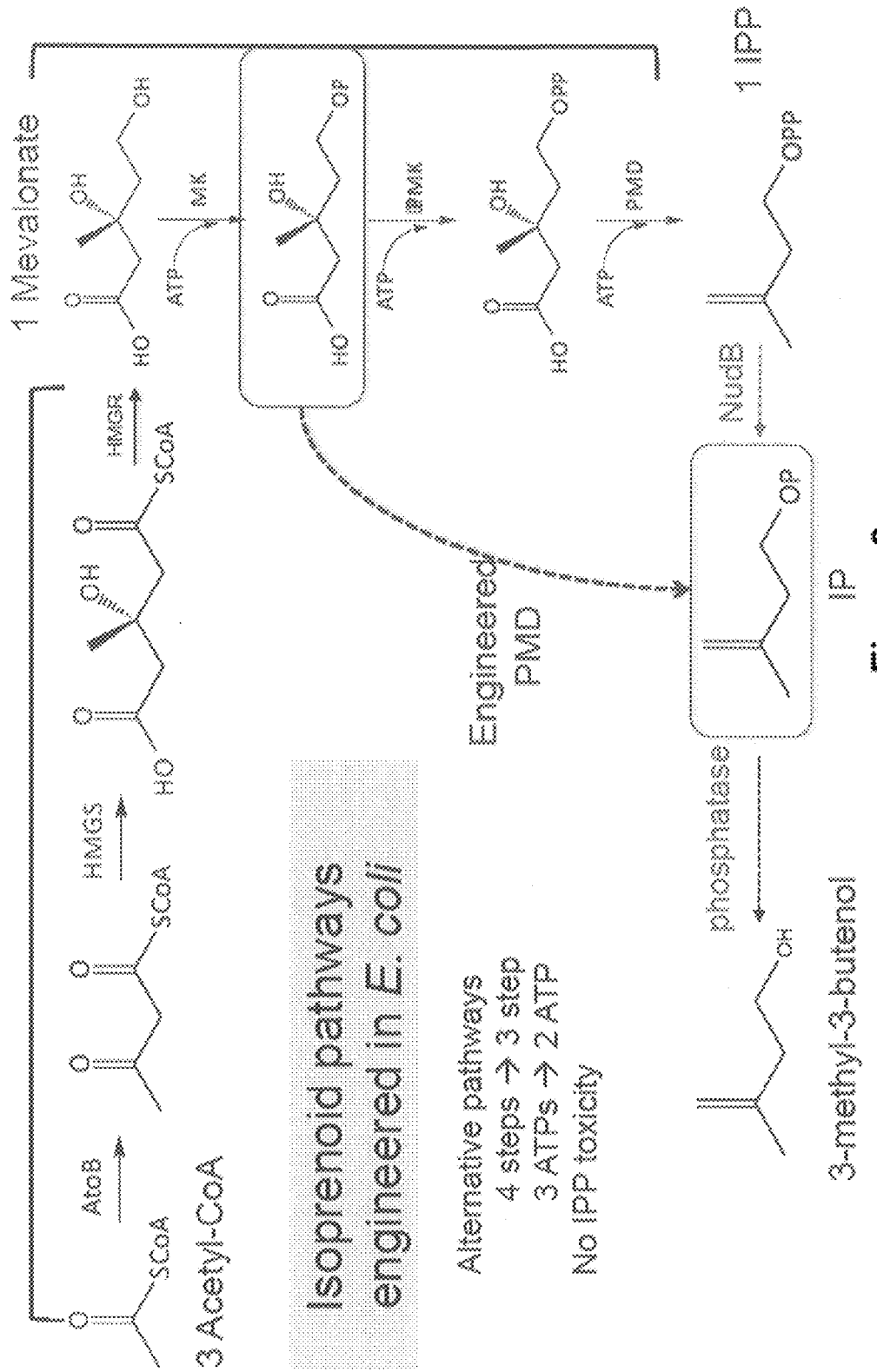
FIG. 3. The second modified pathway for isopentenol production from acetyl CoA. Mevalonate is phosphorylated once by MK, and mevalonate phosphate directly converted to isopentenyl monophosphate (IP) through decarboxylative elimination by PMD (or engineered PMD). IP is dephosphorylated by endogenous phosphatase to generate isopentenol. This modified pathway saves one step and 1 ATP from the original pathway.
Figure 4A:
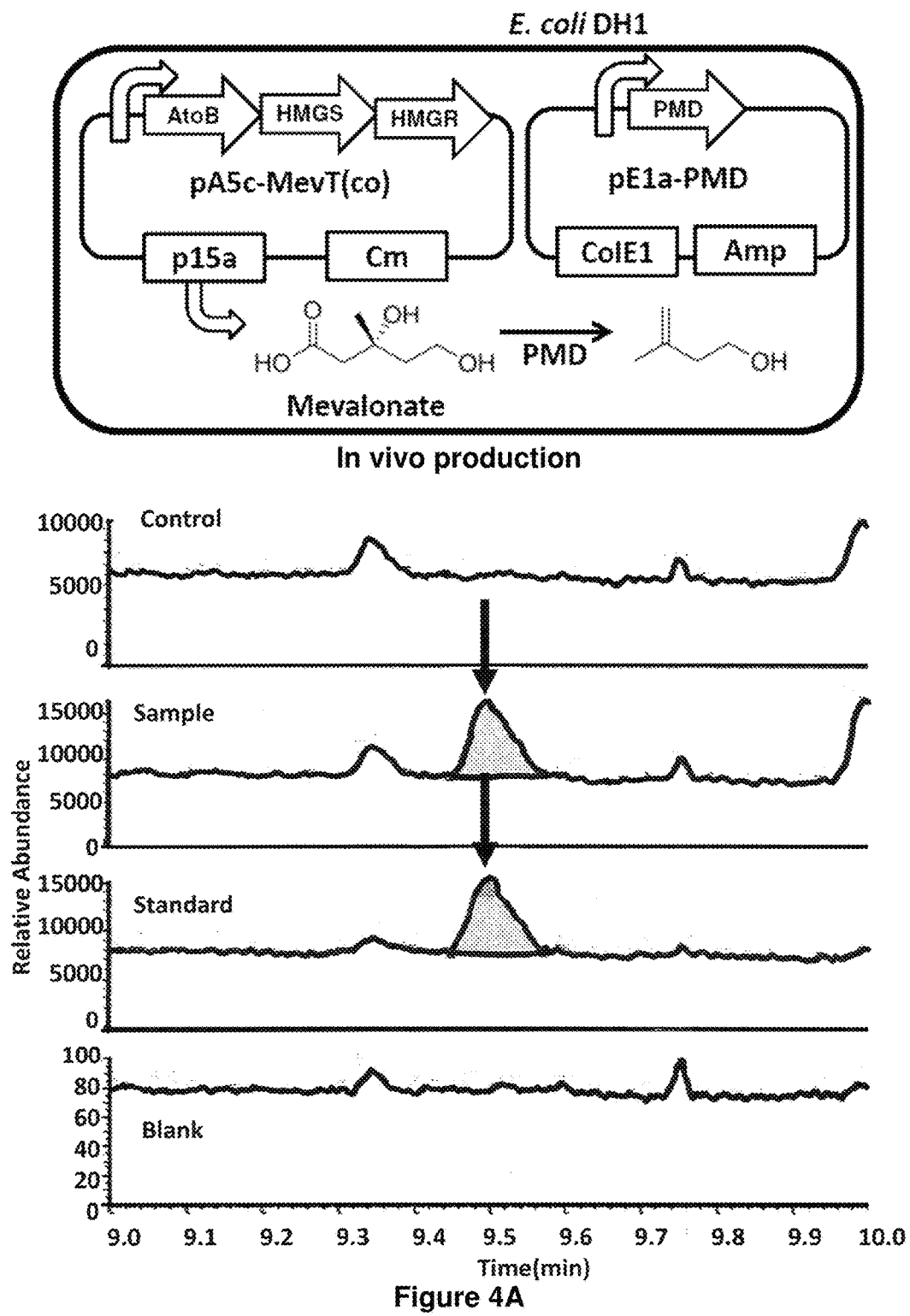
FIG. 4A. In vivo production of isopentenol through the first modified pathway.
Figure 4B:
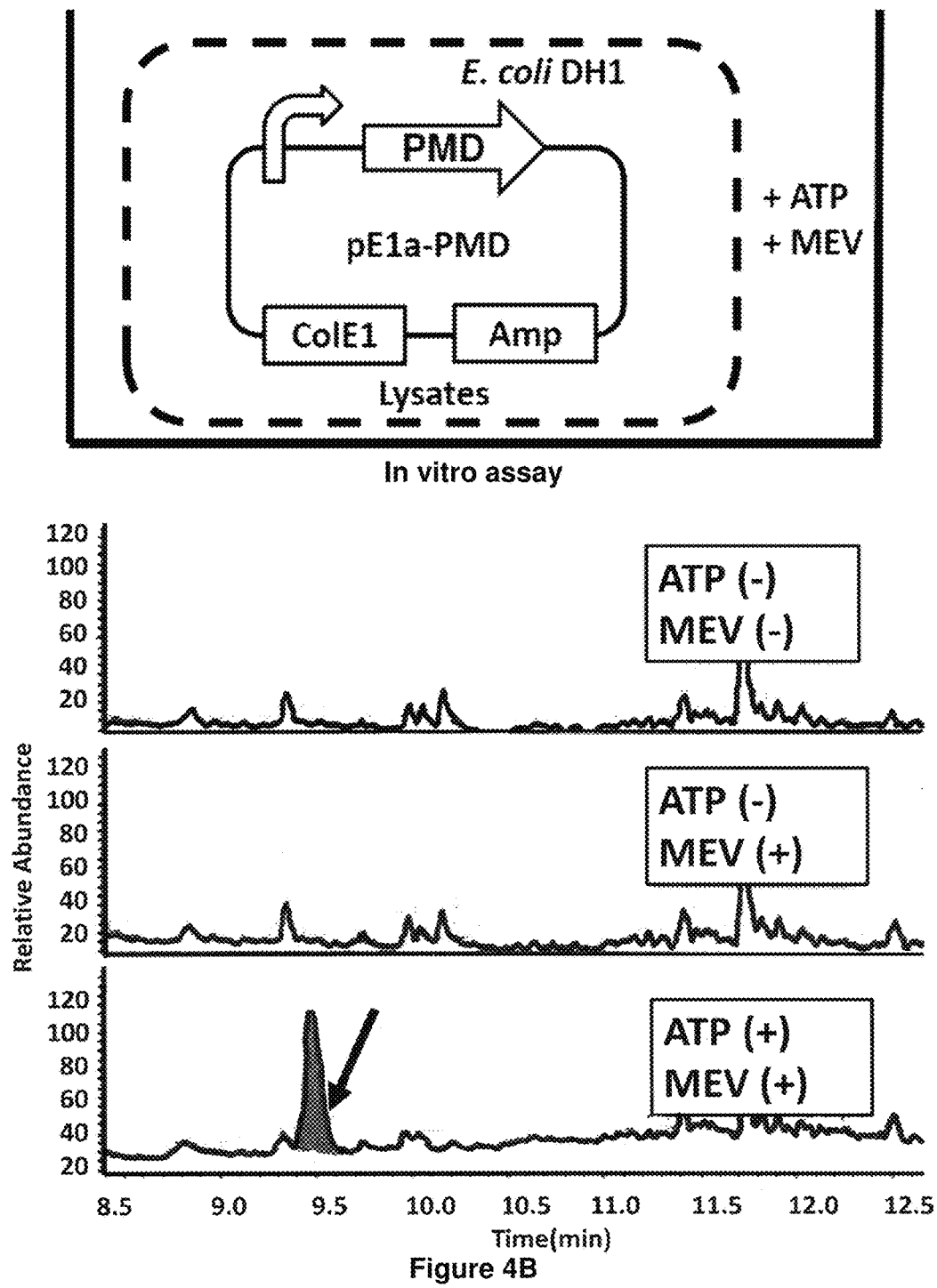
FIG. 4B. IN vitro assay of PMD for direct conversion of mevalonate to isopentenol.
Figure 5:
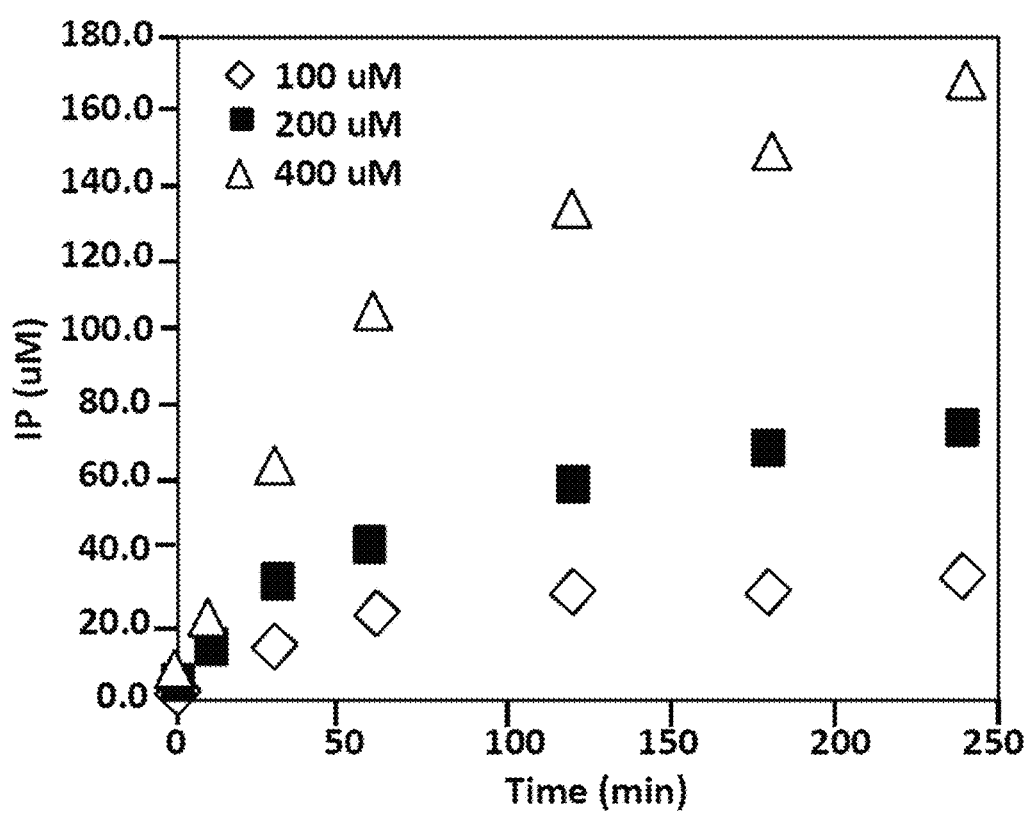
FIG. 5. In vitro formation of isopentenyl monophosphate (IP) from mevalonate phosphate (Mev-P) by PMD. Initial Mev-P concentrations are 100 μM (blue diamond), 200 μM (red square), and 400 μM (green triangle).

FIGS. 1-3 and Table 1 show a comparison of the different pathways.

TABLE 1

|   | PP0 | PP1 | PP2 |
|---|---|---|---|
| ATP | 3 | 1 | 2 |
| # of gene | 7 | 4 | 6 |

Two bypass pathways are constructed. The activity of PMD on MevP is measured in vitro assay. PMD has a promiscuous activity for MevP, but its kinetics are poor (high Km, lower Kcat). In vitro assay showed that PMD decarboxylase MevP. However, its Km for MevP is significantly higher and Kcat for MevP is significantly lower than those for MevPP. This result suggests that decarboxylation of MevP might be the limiting step in the bypass pathway 2. Since we are relying on the promiscuous activity of PMD on MevP, improved activity of PMD for MevP might increase the isopentenol productivity and yield.

Two serine residues in PMD active site are essential for MevP decarboxylation, but not K22 and T209. Active site of PMD is enriched with positively charged amino residues such as arginine and lysine. While the original substrate MevPP has two phosphate resulting the net charge to −4, the alternative substrate mevP has a net charge of −2 and mevalonate has a net charge of 0. To make the active site residues to be more neutral, we have substituted K22 to methionine (neutral residue) and T209 to aspartate (negatively charged) to compensate the decreased negativity of the original substrate. Mutation of K22M and T209D do not significantly change the in vivo production titer.

Production of isopentenol and growth under aerobic condition. Test of different genes from various species. The first heterologous mevalonate pathway is established in E. coli by expressing 5 genes, HMGS, HMGR, MK, PMK and PMD, which are derived from S. cerevisiae for production of amorphadiene. The heterologous mevalonate pathway has been improved by various approaches such as codon-optimization, balancing protein expression levels, etc. We express HMGR and HMGS from different species such as Staphylococcus aureus, Delftia acidovorans and Enterococcus faecalis in addition to Saccharomyces cerevisiae to find the best combination of atoB, HMGS and HMGR together with codon optimized MK and PMD from S. cerevisiae. The result showed that protein expression level and the kinetic properties of homologous enzymes are important for balancing the metabolic pathway, and it depends on the intermediates (via mevalonate or via mevalonate phosphate). We use the best performing strain for the bypass pathway 2 for the rest of studies.

Identification of endogenous phosphatase (knock-out-in vitro experiment) and overexpression of phosphatases. NudB hydrolyzes a phosphate of IPP, producing IP. Subsequently, an endogenous phosphatase hydrolyzes another phosphate from IP, producing Isopentenol. In previous studies, Chou (2013) and George (2014) constructed and optimized the heterologous pathway for isopentenol production. Chou and colleagues determined activity and kinetics of NudB on IPP in vitro. Initially, it was assumed that NudB would hydrolyze diphosphate of IPP since the native activity of NudB is to hydrolyze DHNTP to DHNMP (Gabelli, 2007, Cell). Therefore, kinetics of NudB was determined in vitro by an assay, which includes inorganic pyrophosphatase and phosphate sensor. Since the bypass pathway 2 requires a phosphatase, we question whether the NudB hydrolyze two phosphates sequentially or the diphosphate at once. The in vitro assay results show that NudB hydrolyzed the beta phosphate of IPP, but not the alpha phosphate. Also, NudB do not show the activity of hydrolyzing IP to Isopentenol in vitro. Unexpected activity of NudB is puzzling because it has been observed that in the original pathway, isopentenol production can be improved by enhanced expression of NudB in vivo. This result indicated that there is an endogenous phosphatase that hydrolyze the alpha phosphate from IP produced by the hydrolysis reaction of NudB.

AphA, an alkaline phosphatase, is found to actively hydrolyze IP to Isopentenol. To identify the endogenous phosphatase, we test IP hydrolysis activity of cell lysates of 36 monophosphatase mutants and compared its relative activity with that of wild type. All 36 mutants are retrieved from Keio collection (Baba, MSB), and cell lysates are prepared by culturing mutants in LB. We identify three mutants that produce less IP that other mutants and wild type. These three mutants are subsequently cloned to a vector for overexpression. Expression of three phosphatase are induced by 0.5 mM IPTG, and cell lysates are prepared. Among these three phosphatase, aphA expressed cell lysates show significantly higher and faster hydrolysis activity on IP.

AphA overexpression in vivo do not improve the isopentenol production in the bypass pathway. Next we seek to determine whether overexpression of aphA increases the production of isopentenol in vivo. Overexpression of aphA does not significantly increase the isopentenol production. Given that aphA is expressed in vivo, this result suggests that IP hydrolysis may not be the limiting step in our bypass pathway 2.

Production of isopentenol and growth under anaerobic condition. Initial run of microaerobic fermentation shows that under the oxygen-limiting conditions, glucose are consumed for producing mixed acids such as lactate, formate and acetate. Therefore, we introduce mutants where three fermentation-related genes are deleted and tested whether the bypass pathway 2 performs better under the microaerobic condition than the original pathway. The result shows that the bypass pathway in three knock out mutants produced higher mg/L isopentenol than the original pathway under microaerobic condition.

In vitro assay shows that hydrolysis of isopentenyl monophosphate can be a limiting step if decarboxylation step is not the rate-limiting reaction. To identify the endogenous phosphatase, which hydrolyze the isopentenyl monophosphate producing isopentenol, we have screened 36 endogenous monophosphatase mutants of E. coli. Initial screening showed that three mutants produced less isopentenol compared to that of the wild type, and over-expression of one of the three phosphatase genes resulted in much faster conversion of isopentenyl monophosphate to isopentenol compared to other two phosphatase genes.

Based on our initial works, the modified pathway that doesn't have PMK and NudB produced about 900 mg/L of isopentenol after 42 hrs incubation, which is 40% higher than the titer from the original pathway under aerobic condition (640 mg/L). Also, cells with the modified pathway showed better growth giving the final OD of above 3.5, while the E. coli strains with the original pathway resulted in OD about 2.7 under aerobic condition. Under anaerobic condition, advantages of the bypass pathway has been inconclusive, but cells with the modified pathway showed a better growth, resulting about 28% higher OD than those with the original pathway.

Biological production of higher alcohols such as isopentenol has been extensively investigated, but major bottleneck of industrialization has been a cost-effectiveness of the biological production system in fermentor scale. This new pathways can be used in a fermentor scale, even under anaerobic or microanaerobic conditions to produce isopentenol in *E. coli*.

Example 2

Advanced Pathways for Microbial Production of Branched C$_5$ Alcohols

Project Goals: The Joint BioEnergy Institute (JBEI) aims to produce a chemically diverse suite of biofuels from lignocellulosic biomass. Isoprenoid-based biofuels have been of great interest due to their superb fuel properties such as low freezing temperature and high octane number. Mevalonate (MVA) pathway is one of the major biosynthetic pathways of isoprenoid fuel production, and the engineering of this pathway is a key approach to achieve higher production of these biofuels. Various engineering strategies and tools have been explored to identify the bottlenecks of the pathway and to understand the pathway enzymes better, but the intrinsic energy demands of this pathway and the operational cost for aeration to meet the energy demands have been still a problem when a production in large scale using fermentor is exploited. In this work, we present modified version of the MVA pathway that will address these issues for isoprenoid biofuel production.

Isoprenoids are considered as one of the most promising advanced biofuels. Among the isoprenoid compounds, branched five carbon (C$_5$) alcohols have been tested as good biofuel compounds with favorable combustion properties and octane numbers to gasoline. A synthetic pathway for C$_5$ alcohols production has been reported previously in *E. coli* using the heterologous MVA pathway (Chou and Keasling, 2012), and further metabolic engineering efforts on this synthetic pathway have led to about 50% theoretical yield in the C$_5$ alcohol production (George et al. 2014).

Even though the MVA pathway has been known to be less efficient than the methylerythritol phosphate (MEP) pathway in carbon and redox balance as well as in energy balance, the MVA pathway has been extensively used for microbial production of a range of valuable isoprenoids due to its tractability and the high titers it can provide. However, the energy demands of this pathway and the operational cost for aeration to meet these energy demands have been a problem, especially when a production in large scale using fermentor is exploited. Modified pathways for C$_5$ alcohol production, of the present invention, address these issues of the traditional MVA pathways.

Host cells with advanced pathways for C$_5$ alcohol production is engineered that reduce cellular costs for isopentenol production. One of the modified pathways showed that isopentenol could be produced via decarboxylation of mevalonate monophosphate to isopentenyl monophosphate by the promiscuous activity of the decarboxylase. The titer and the growth of the engineered strains with this modified pathway are better than those with the original pathway, and the efficiency of this modified pathway is tested under microaerobic condition. The decarboxylase enzyme engineering and the pathway optimization of this modified pathway leads to a microbial C$_5$ alcohol production more economically feasible, especially for large scale industrial application.

References cited in Example 2:

Chou, H. H., Keasling, J. D., Synthetic pathway for production of five-carbon alcohols from isopentenyl diphosphate. *Appl. Environ. Microbiol.* 2012, 78, 7849-7855

George, K. W., Chen, A., Jain, A., Batth, T. S., Baidoo, E., Wang, G., Adams, P. D., Petzold, C. J., Keasling, J. D., Lee, T. S., Correlation analysis of targeted proteins and metabolites to assess and engineer microbial isopentenol production, *Biotech. Bioeng.* 2014, 111, 1648-1658

Example 3

Isopentenyl Diphosphate (IPP)-Bypass Mevalonate Pathways for Isopentenol Production Branched C$_5$ alcohols are promising biofuels with favorable combustion properties. A mevalonate (MVA)-based isoprenoid biosynthetic pathway for C$_5$ alcohols is constructed in *Escherichia coli* using genes from several organisms, and the pathway is optimized to achieve over 50% theoretical yield. Although the MVA pathway is energetically less efficient than the native methylerythritol 4-phosphate (MEP) pathway, implementing the MVA pathway in bacterial hosts such as *E. coli* is advantageous due to its lack of endogenous regulation. The MVA and MEP pathways intersect at isopentenyl diphosphate (IPP), the direct precursor to isoprenoid-derived C$_5$ alcohols and initial precursor to longer chain terpenes, which makes independent regulation of the pathways difficult. In pursuit of the complete "decoupling" of the MVA pathway from native cellular regulation, novel IPP-bypass MVA pathways are designed for C$_5$ alcohol production by utilizing promiscuous activities of two enzymes, phosphomevalonate decarboxylase (PMD) and an *E. coli*-endogenous phosphatase (AphA). These bypass pathways have reduced energetic requirements, are further decoupled from intrinsic regulation, and are free from IPP-related toxicity. In addition to these benefits, it is demonstrate that reduced aeration rate has less impact on the bypass pathway than the original MVA pathway. Finally, it is showed that performance of the bypass pathway is primarily determined by the activity of PMD. PMD mutants are designed with improved activity and demonstrated titer increases in the mutant strains. These modified pathways are a good platform for industrial production of isopentenol and related chemicals such as isoprene.

1. Introduction

Isopentenol (3-methyl-3-buten-1-ol) is a potential biofuel and important precursor for flavor compounds (prenols and isoamyl alcohol esters) and industrial chemicals such as isoprene (Chou and Keasling, 2012 and Peralta-Yahya et al., 2012). Two classes of metabolic pathways have been engineered to produce isopentenol in microbial hosts: amino acid production pathways utilizing 2-keto-acid intermediates (Connor and Liao, 2008 and Connor et al., 2010), and isoprenoid biosynthesis pathways, including both the mevalonate (MVA) (Chou and Keasling, 2012, Withers et al., 2007, George et al., 2014 and Zheng et al., 2013) and non-mevalonate pathway (methylerythritol 4-phosphate (MEP) or 1-deoxy-D-xylulose 5-phosphate (DXP) pathway) (Liu et al., 2013). A heterologous MVA pathway was constructed to produce isopentenol in *Escherichia coli* by expressing 7 genes (FIG. 12—Pathway O) (Chou and Keasling, 2012). To produce isopentenol, IPP is hydrolyzed by phosphatases such as NudF from *Bacillus subtilis* or NudB from *E. coli*. Although the initial performance of this pathway was low (8.3% of pathway-dependent theoretical yield), subsequent optimization has significantly improved yields and titers (George et al., 2014 and Zheng et al., 2013). Most recently, isopentenol was produced at a titer of 2.2 g/L from 10 g/L glucose, which is almost 70% of apparent theoretical yield (George et al., 2015).

A variety of engineering strategies have been applied to optimize the heterologous MVA pathway and improve isoprenoid production in *E. coli* (Pfleger et al., 2006; Anthony et al., 2009; Dueber et al., 2009; Redding-Johanson et al., 2011; Dahl et al., 2013; Zhu et al., 2014). In each case, balanced expression of pathway enzymes was required to maximize flux towards final products while minimizing the accumulation of toxic intermediates such as farnesyl diphosphate (FPP) (Martin et al., 2003), IPP (Withers et al., 2007, George et al., 2014, Zheng et al., 2013 and Martin et al., 2003), and 3-hydroxy-3-methyl-glutaryl-CoA (HMG-CoA) (Pitera et al., 2007). For isopentenol production, the careful management of IPP levels is critical: engineering strategies to address its accumulation have included the deliberate "tuning" of the upstream MVA pathway (George et al., 2014) and the extensive overexpression of NudB, the phosphatase required to transform IPP into isopentenol (George et al., 2015).

Although the mechanism of IPP toxicity is unknown, the deleterious effects of its accumulation are clear. First, it has been demonstrated in various studies that accumulation of IPP inhibits cell growth (Withers et al., 2007, George et al., 2014 and Martin et al., 2003), which prevents a bioprocess from achieving enough cell biomass to maximize product titer. Even prior to affecting cell growth, it is likely that the transient accumulation of IPP induces a variety of stress responses as has previously been observed during the accumulation of FPP (Dahl et al., 2013). Responses to both generalized (e.g., RpoS-induced (Hengge, 2008)) and condition-specific stress (e.g., acid stress (Sun et al., 2011), oxidative stress (Adolfsen and Brynildsen, 2015) and osmotic stress (Cohen, 2014)) result in the recruitment of ATP-dependent defense mechanisms including DNA repair (Sun et al., 2011 and Adolfsen and Brynildsen, 2015), ATPases (Sun et al., 2011), and ABC transporters (Cohen, 2014). The ATP cost of these processes may serve to compete with the energetically-expensive MVA pathway, reducing the yield and productivity of isoprenoid production. In the case of isopentenol production, high flux to IPP has an additional detrimental impact: through the action of *E. coli* native IPP isomerase (Idi), IPP can be diverted by native isoprenoid pathways that produce $C_{10}$- and $C_{15}$- prenyl diphosphates (i.e. geranyl diphosphate (GPP) and FPP). The production of GPP and FPP decreases the carbon utilization efficiency of isopentenol production, and potentially inhibits MK activity, which in turn reduces MVA flux to the downstream enzyme reactions (Ma et al., 2011). Moreover, isopentenol production via IPP requires the energetically expensive ATP-consuming formation of diphosphate prior to enzymatic hydrolysis. This diphosphate formation and subsequent hydrolysis is considerably inefficient in terms of atom and energy economy. Due to these factors, the "IPP-dependency" of the MVA pathway may intrinsically limit the engineering of the MVA pathway for more efficient isopentenol production.

Isopentenol production is decoupled from IPP formation by constructing two novel "IPP-bypass" pathways. These two IPP-bypass pathways rely on decarboxylation of either MVA or MVA monophosphate (MVAP) for isopentenol production and do not produce IPP as an essential precursor for isopentenol. These optimized pathways eliminate the negative effects of IPP accumulation such as growth inhibition, energy-consuming stress responses, diverted carbon flux, and regulatory inhibition on mevalonate kinase (MK). It is envisioned that these two IPP-bypass pathways could open a new dimension of engineering the MVA pathway to produce isopentenol and isopentenol-derived valuable compounds such as isoprene.

2. Materials and Methods 2.1. Strains and Plasmid Construction

All strains and plasmids used in this study are listed in Table 2. Throughout Example 3, *E. coli* BW25113 strain is used for isopentenol production, and *E. coli* DH10B is used for genetic cloning. The original sequence of $PMD_{hv}$ is obtained from NCBI database (HVO_1412, NC_013967.1), codon-optimized for expression in *E. coli* by GenScript (New Jersey, USA), and the optimized sequence is synthesized by IDT (Iowa, USA). A plasmid coding $PMD_{se}$ is received from Dr. Miziorko at University of Missouri (Barta et al., 2012), and the coding sequence is amplified by PCR for sub-cloning to expression vectors.

TABLE 2

List of strains and plasmid described herein.

| | Description | Reference |
|---|---|---|
| Strains | | |
| ΔaphA | *E. coli* K12 BW25113 ΔaphA | Keio Collection (Baba et al., 2006) |
| Δagp | *E. coli* K12 BW25113 Δagp | Keio Collection (Baba et al., 2006) |
| ΔyqaB | *E. coli* K12 BW25113 ΔyqaB | Keio Collection (Baba et al., 2006) |
| ARK1a | JBEI-12056 + JBEI-9348 | This study |
| ARK1b | JBEI-6824 + JBEI-9348 | This study |
| ARK1c | JBEI-6831 + JBEI-9348 | This study |
| ARK1d | JBEI-7575 + JBEI-9348 | This study |
| ARK1e | JBEI-6818 + JBEI-6833 | This study |
| ARK1f | JBEI-6818 + JBEI-6834 | This study |
| ARK2a | JBEI-9310 + JBEI-9314 | This study |
| ARK2b | JBEI-9309 + JBEI-9314 | This study |
| ARK2c | JBEI-9312 + JBEI-9314 | This study |
| ARK2d | JBEI-9311 + JBEI-9314 | This study |
| ARK2e | JBEI-12051 + JBEI-9314 | This study |
| ARK2f | JBEI-12051 + JBEI-12064 | This study |
| ARK2aa | JBEI-12050 + JBEI-9314 | This study |
| ARK2a$_{M1}$ | JBEI-9310 + JBEI-12060 | This study |
| ARK2a$_{M2}$ | JBEI-9310 + JBEI-12061 | This study |
| ARK2a$_{M3}$ | JBEI-9310 + JBEI-12062 | This study |
| ARK3a | JBEI-3100 + JBEI-12229 | This study |
| ARK3b | JBEI-3100 + JBEI-3277 | This study |
| ARK4 | JBEI-9310 + JBEI-12054 | This study |

TABLE 2-continued

List of strains and plasmid described herein.

| | Description | Reference |
|---|---|---|
| ARK5 | JBEI-9310 + JBEI-12059 | This study |
| Plasmids | | |
| JBEI-6818 | pBbA5c-MevTo-MKco-PMKco | (George et al., 2014) |
| JBEI-6824 | pBbA5c-MevTco-BBa1002-pTrc-MKco-PMKco | (George et al., 2014) |
| JBEI-6831 | pBbA5c-MTSA-BBa1002-pTrc-MKco-PMKco | (George et al., 2014) |
| JBEI-6833 | pTrc99a-NudB-PMDsc | (George et al., 2014) |
| JBEI-6834 | pTrc99a-NudB-PMDsc-Mkco | (George et al., 2014) |
| JBEI-7575 | pBbA5c-MTDA-BBa1002-pTrc-MKco-PMKco | Gift from Eunmi Kim |
| JBEI-9309 | pBbA5c-MevTco-BBa1002-pTrc-MKco | This study |
| JBEI-9310 | pBbA5c-MevTo-BBa1002-pTrc-MKco | This study |
| JBEI-9311 | pBbA5c-MTDA-BBa1002-pTrc-MKco | This study |
| JBEI-9312 | pBbA5c-MTSA-BBa1002-pTrc-MKco | This study |
| JBEI-9314 | pTrc99a-PMDsc | This study |
| JBEI-9348 | pTrc99a-PMDsc-NudB | This study |
| JBEI-12050 | pBbA5c-MevTo-BBa1002-pTrc-MKco-aphA | This study |
| JBEI-12051 | pBbA5c-MevTo-MKco | This study |
| JBEI-12052 | pSKB3-PMDsc | This study |
| JBEI-12053 | pSKB3-PMDsc_K22M | This study |
| JBEI-12054 | pTrc99a-PMDse | This study |
| JBEI-12055 | pSKB3-PMDsc_T209D | This study |
| JBEI-12056 | pBbA5c-MevTo-BBa1002-pTrc-MKco-PMKco | This study |
| JBEI-12057 | pSKB3-PMDsc_R74H | This study |
| JBEI-12058 | pSKB3-PMDsc_I145F | This study |
| JBEI-12059 | pTrc99a-PMDhv | This study |
| JBEI-12060 | pTrc99a-PMDsc_R74H | This study |
| JBEI-12061 | pTrc99a-PMDsc_I145F | This study |
| JBEI-12062 | pTrc99a-PMDsc_R74H/I145F | This study |
| JBEI-12064 | pTrc99a-PMDsc-MKco | This study |
| JBEI-12229 | pE1a-PMDsc | This study |

2.2. Protein Expression and Purification

A plasmid encoding a wild type mevalonate diphosphate decarboxylase from *Saccharomyces cerevisiae* ($PMD_{sc}$) with N-terminal His-tag (pSKB3-$PMD_{sc}$) is transformed into *E. coli* BL21 (DE3). A seed culture of BL21 (DE3) harboring pSKB3-$PMD_{sc}$ is prepared by inoculating a single colony and growing it overnight in Luria-Bertani (LB) medium containing kanamycin (50 μg/mL). The seed culture is diluted in Terrific Broth supplemented with 2% glycerol and 50 μg/mL kanamycin and incubated at 37° C. until the optical density of the culture at 600 nm ($OD_{600}$) reached to 0.6-0.8. The cell culture is supplemented with isopropyl-β-D-thiogalactopyranoside (IPTG) to the final concentration of 0.5 mM and transferred to 18° C. for protein expression overnight. Cells are collected by centrifugation and re-suspended in 50 mM Tris-HCl (pH 7.5) buffer containing 300 mM NaCl and 10 mM imidazole. Cells are lysed by sonication and purified by HisPur Cobalt Resins (Thermo Scientific, USA). The purified $PMD_{sc}$ is desalted in 10 mM Tris-HCl (pH 7.5) containing 50 mM NaCl, 0.5 mM dithiothreitol (DTT) and 20% glycerol, and flash-frozen in liquid nitrogen for storage at −80° C. All $PMD_{sc}$ mutants, $PMD_{se}$, and NudB are purified as described above, except that NudB is desalted in 50 mM Tris-HCl (pH 8.0) buffer containing 0.1 mM EDTA, 1 mM DTT and 20% glycerol.

2.3. Enzyme Characterization and Kinetics

In vitro enzyme kinetics of decarboxylases are performed as described in previous studies (Barta et al., 2012 and Vannice et al., 2014). Briefly, enzymatic activity of decarboxylase is determined by a spectrophotometer assay quantifying ADP product formation, which is coupled to NADH oxidation by pyruvate kinase/lactate dehydrogenase. Assay mixtures are prepared in 50 mM HEPES-KOH (pH 7.5) containing 10 mM $MgCl_2$, 400 μM phosphoenolpyruvate, 200 μM NADH, 4 mM ATP, and 25 U of pyruvate kinase/lactate dehydrogenase (Sigma, P0294). The reaction is initiated by addition of various concentrations of MVAP from 100 μM to 4,000 μM, and the reaction velocity is determined by monitoring OD at 340 nm in Spectramax 384 plus microplate reader (Molecular Devices, USA).

2.4. Isopentenol Production in *E. coli*

*E. coli* BW25113 harboring two plasmids is used for isopentenol production. Seed cultures of all production strains are prepared by growing single colonies in LB medium containing 100 μm/mL ampicillin and 30 μg/mL chloramphenicol overnight at 37° C. with shaking at 200 rpm. The seed cultures are diluted in EZ-Rich defined medium (Teknova, USA) containing 10 g/L glucose (1%, w/v), 100 μg/mL ampicillin and 30 μg/mL chloramphenicol. The *E. coli* cell cultures are incubated in rotary shakers (200 rpm) at 37° C., and 0.5 mM IPTG is added to induce protein expression at $OD_{600}$ of 0.6-0.8. To provide different levels of aeration, identical volumes of the cell culture are split into two flasks for incubation at 30° C. with shaking at either 200 rpm or 30 rpm.

For isopentenol quantification, 250 μL of cell culture is combined with 250 μL of ethyl acetate containing 1-butanol (30 mg/L) as an internal standard. This mixture of ethyl acetate and cell culture is vigorously shaken for 15 min and subsequently centrifuged at 13,000 g for 2 min to separate ethyl acetate from the aqueous phase. 100 μL of the ethyl acetate layer was diluted 5-fold, and 1 μL is analyzed by Agilent GCMS equipped with Cyclosil-B column (Agilent, USA) or Thermo GCFID equipped with DB-WAX column (Agilent, USA) for quantitation of isopentenol.

2.5. Phosphatase Screening

To identify IP-hydrolyzing endogenous phosphatases, single gene knockout mutants of 36 phosphatases, of which substrates are mostly mono-phosphorylated metabolites, are retrieved from the Keio collection (Baba et al., 2006). 1 mL overnight cultures from each mutant are concentrated in 0.5 mL of 50 mM Tris-HCl (pH 8.0) buffer containing 1 mM DTT and ~50 mg of glass beads (<100 µm, Sigma-Aldrich, USA). Cells are lysed by bead-beating for 2 min at 6.0 M/s (MP biomedicals Fast Prep, USA). After centrifugation of cell lysates at 20,000 g for 10 min, clear supernatant is used for assay reaction containing 0.5 mM isopentenyl monophosphate (IP). An equal volume of ethyl acetate is added to 100 µL of assay reaction after incubating overnight at 30° C., and isopentenol is extracted for 10 min by vigorous mixing.

Coding sequences of agp, aphA, and yqaB are amplified from BW25113 genome by PCR, and they are subsequently cloned to pBbE1a vector (Lee et al., 2011) for over-expression. Expression of these three genes are induced by addition of 0.5 mM IPTG to the cell cultures, and cell lysates of each sample are prepared with three biological replicates as described above for screening of the 36 mutants. 600 µL of assay reactions containing cell lysates, 1 mM DTT are prepared and the reaction is initiated by addition of 0.5 mM IP. At each time point (0, 1, 3, 6 and 22 h), 100 µL of the reaction mixture is sampled and combined with 100 µL of ethyl acetate to extract isopentenol.

2.6. Quantification of Metabolites

All metabolites are analyzed by liquid chromatography mass spectrometry (LC-MS; Agilent Technologies 1200 Series HPLC system and Agilent Technologies 6210 time-of-flight mass spectrometer) on a ZIC-HILIC column (150 mm length, 2.1-mm internal diameter, and 3.5-µm particle size). Standard chemicals (IPP and IP) are purchased from Sigma-Aldrich (USA). Metabolites are eluted isocratically with a mobile phase composition of 64% (v/v) acetonitrile containing 50 mM ammonium acetate with a flow rate of 0.15 mL/min. IPP and IP from *E. coli* extracts or enzyme assay are quantified via eight-point calibration curves ranging from 781.25 nM to 200 µM.

3. Results and Discussions 3.1. Design Rationale for IPP-Bypass Isopentenol Pathways The biosynthesis of IPP from MVA consists of three energy-consuming reactions: two kinases (MK and phosphomevalonate kinase (PMK)) result in the formation of diphosphomevalonate (MVAPP), which is subsequently transformed by a decarboxylase (PMD) to form IPP. The diphosphate group of IPP is essential in chain elongation to produce GPP and FPP, and in the carbocation formation to produce cyclic terpenes since the removal of the diphosphate group is thermodynamically-favorable (Degenhardt et al., 2009). In isopentenol production via the MVA pathway, the alcohol is also produced by removal of the diphosphate group of IPP. However, this reaction is different from carbocation formation and does not require the diphosphate group as an essential leaving group to drive the hydrolysis reaction. Therefore, formation of the diphosphate group and its subsequent removal make the overall MVA pathway for isopentenol inefficient by unnecessarily consuming two ATPs.

Figure 12:
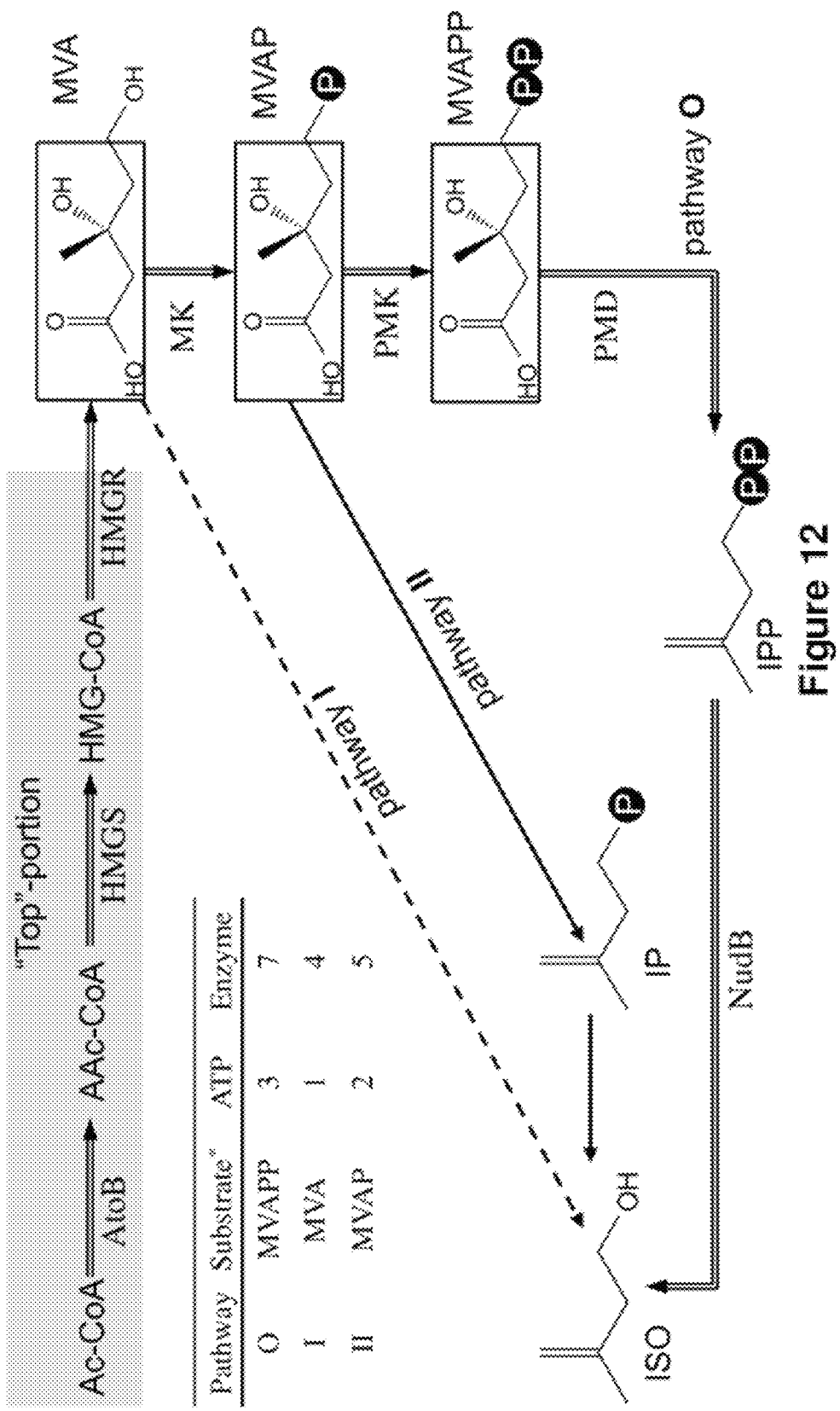
FIG. 12. Original and two modified mevalonate pathways for isopentenol production. The original mevalonate pathway (pathway O) produces isopentenyl diphosphate (IPP), which is dephosphorylated by NudB, as an intermediate. Two modified pathways: direct decarboxylation of mevalonate (pathway I) or decarboxylation of mevalonate diphosphate (pathway II) followed by de-phosphorylation of isopentenyl monophosphate (IP). Numbers of ATP and enzymes required for each pathway are summarized in the table. Ac-CoA, acetyl-CoA; AAc-CoA, acetoacetyl-CoA; HMG-CoA, 3-hydroxy-3-methyl-glutaryl-CoA; PMK, phosphomevalonate kinase; PMD, phosphomevalonate decarboxylase).

To address the energetic limitations of IPP formation—and the deleterious effects of its accumulation—we designed two modified isopentenol pathways that bypass the formation of IPP (FIG. 12). The first modified pathway (pathway I) is designed for the direct conversion of MVA to isopentenol via ATP-driven decarboxylative elimination, and the second pathway (pathway II) is designed for a decarboxylative elimination of MVAP to IP followed by the hydrolysis of IP to isopentenol (FIG. 12). These modified pathways result in IPP-independent isopentenol production, which could relieve toxicity and prevent the loss of IPP flux to native pathways such as ubiquinone biosynthesis. Moreover, these two pathways reduce the complexity and energy cost of isopentenol production. As shown in FIG. 12, direct decarboxylation of MVA (pathway I) reduces the number of enzymes required from 7 to 4 and the ATP requirement per molecule of isopentenol from 3 to 1. In IPP-bypass pathway II, the number of enzymes is reduced from 7 to 5 and ATP molecules from 3 to 2 compared to the original pathway. Given the potential benefits of pathways I and II over the original MVA pathway (pathway O), options to construct and express these optimized pathways in *E. coli* to produce isopentenol are explored.

3.2. Engineering of IPP-Bypass Pathway I and Identification of Promiscuous Decarboxylase Activity Toward MVA and MVAP Engineering IPP-bypass pathways I and II requires a decarboxylase that converts MVA or MVAP to isopentenol or IP, respectively. Based on the chemical structures of the substrates and products (FIG. 1) and proposed mechanism of the decarboxylation reaction, it is hypothesized that PMD might serve as a decarboxylase for MVA and MVAP in addition to its native substrate, MVAPP. Since PMD from *S. cerevisiae* ($PMD_{sc}$) has been widely used for isoprenoid production in engineered *E. coli* (George et al., 2014, Zheng et al., 2013, Alonso-Gutierrez et al., 2013, Kim et al., 2015 and Wang et al., 2010), $PMD_{sc}$ is initially chosen as the target PMD enzyme for each bypass pathway. $PMD_{sc}$ was previously reported to convert 3-hydroxy-3-methylbutyrate (3-HMB) to isobutene (Gogerty and Bobik, 2010), which supports the hypothesis that this enzyme has promiscuous decarboxylase activity.

Figure 13A:
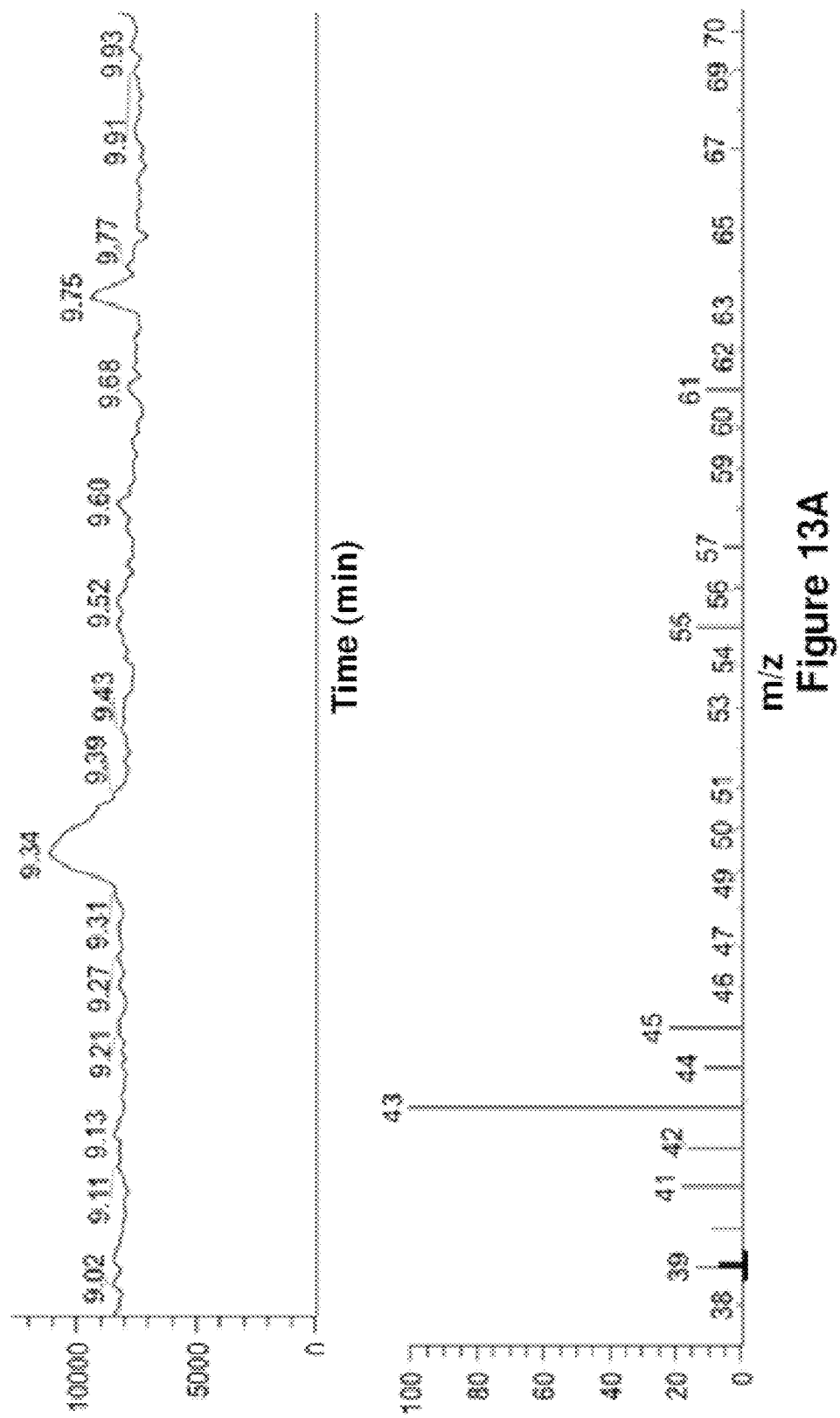
FIG. 13A. GC/MS chromatogram (top) and mass spectra (bottom) of ethyl acetate-extracted metabolites detected from control strain with three genes (ARK3a; atoB, HMGS, HMGR).
Figure 13B:
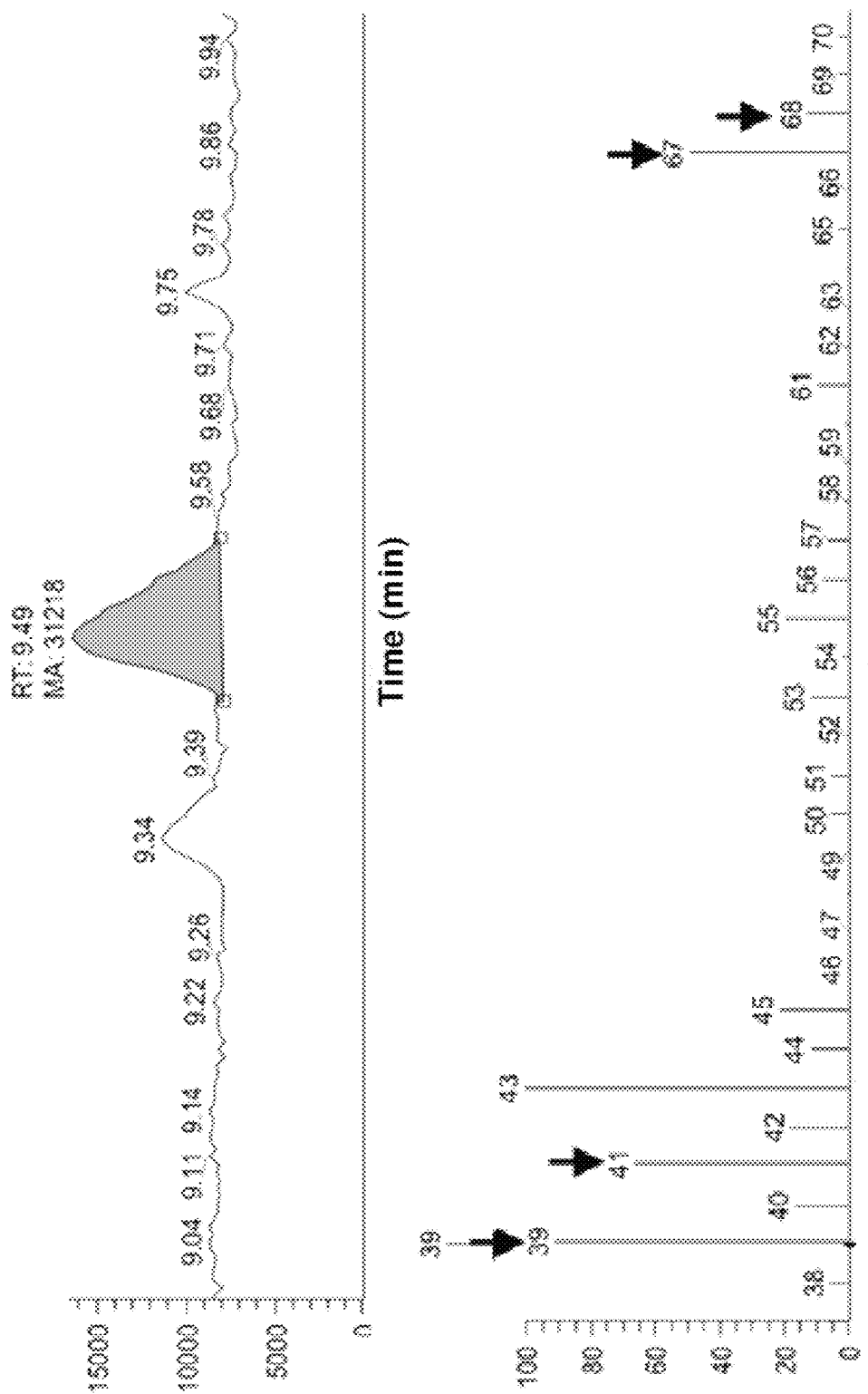
FIG. 13B. GC/MS chromatogram (top) and mass spectra (bottom) of ethyl acetate-extracted metabolites detected from engineered strains with four genes (ARK3b; atoB, HMGS, HMGR and $PMD_{sc}$). The mass spectrum of the peak that eluted at 9.49 min detected in ARK3b is very similar to that of the isopentenol standard (FIG. 13C), and is not present in the ethyl acetate blank (FIG. 13D). Arrows indicate masses of the peak at retention time of 9.49 min detected from both standard (FIG. 13C) and the engineered strain (this figure; ARK3b).
Figure 13C:
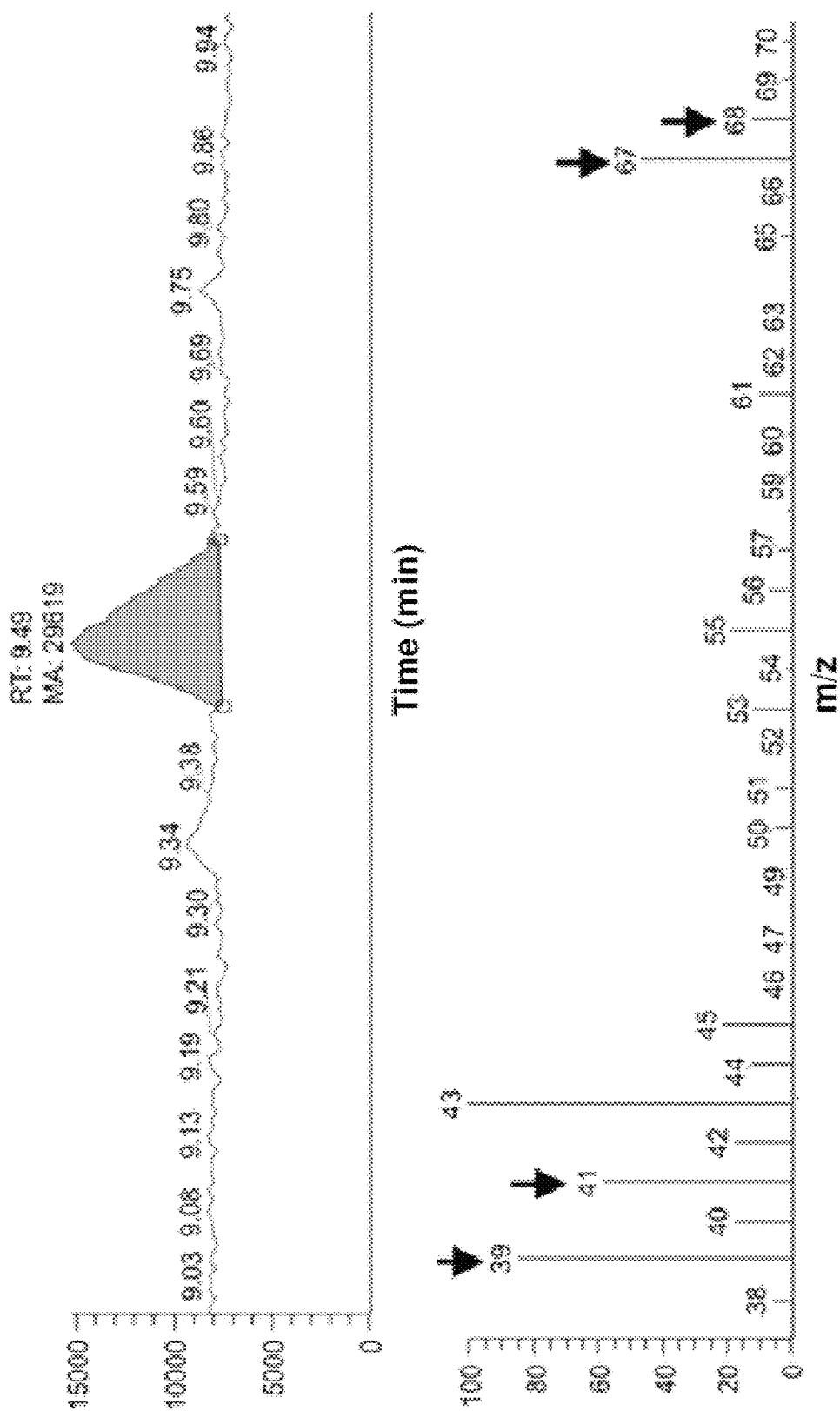
FIG. 13C. GC/MS chromatogram (top) and mass spectra (bottom) of the isopentenol standard.
Figure 13D:
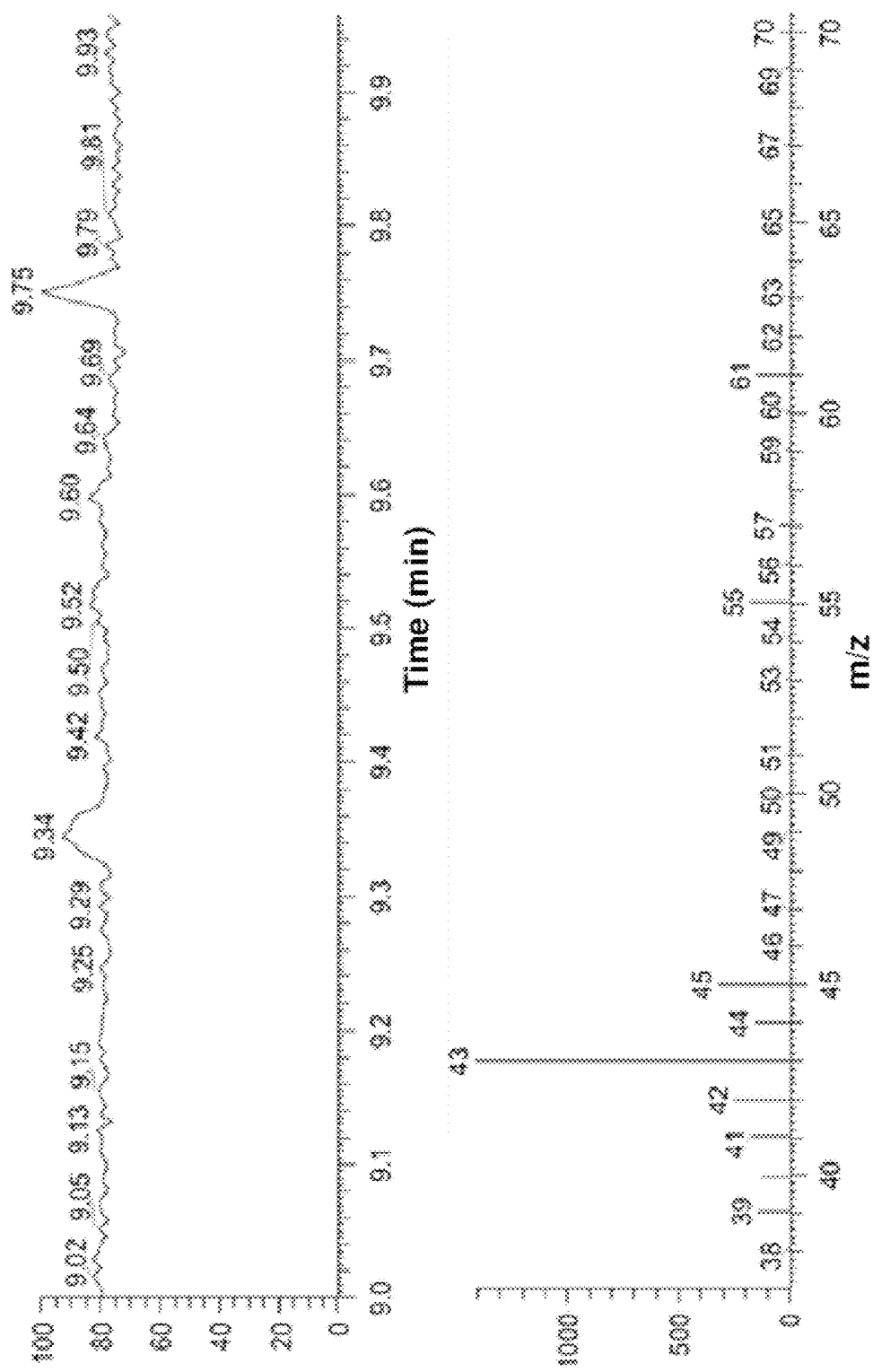
FIG. 13D. GC/MS chromatogram (top) and mass spectra (bottom) of the ethyl acetate blank.

With $PMD_{sc}$ as a potential decarboxylase for MVA, IPP-bypass pathway I is first constructed in *E. coli* by expressing three enzymes (AtoB, HMGS, and HMGR) to produce MVA along with $PMD_{sc}$ (strain ARK3a, Table 2). When the strain is tested in vivo, the engineered *E. coli* produced 0.85±0.18 mg/L isopentenol (FIG. 13B) while the control strain, which expressed only AtoB, HMGS, and HMGR without $PMD_{sc}$ (strain ARK3b, Table 2) does not show any detectable level of isopentenol (FIG. 13A). The fragmentation pattern and retention time of the isopentenol peak detected in strain ARK3a match those from a 3-methyl-3-buten-1-ol standard (FIG. 13C). In vitro activity measurement is attempted to determine the kinetic parameters of $PMD_{sc}$ for MVA, but the enzyme activity is too low to determine the kinetic parameters (data not shown).

Structural analysis of a homologous PMD from *Staphylococcus epidermis* ($PMD_{se}$) (Barta et al., 2012) suggest that the diphosphate group is important for substrate binding even though it is not directly involved in the catalytic decarboxylation reaction. The importance of the diphosphate group in $PMD_{se}$ activity implies that the monophosphorylated substrate (i.e. MVAP) might be better suited for decarboxylation than the substrate without any phosphate group (i.e. MVA).

3.3. Engineering of IPP-Bypass Pathway II and Pathway Optimization in *E. coli*

To verify the improved activity of $PMD_{sc}$ for phosphorylated substrates (MVAP), an in vitro assay is performed with both MVA and MVAP. While isopentenol is not detected in the in vitro reaction, a detectable amount of IP is produced when MVAP is used as a substrate for $PMD_{sc}$. This result indicates that $PMD_{sc}$ has higher decarboxylase activity towards MVAP than MVA and suggests that the phosphate group of MVAP does indeed enhance substrate binding and catalysis. The $k_{cat}$ (0.14 s$^{-1}$) and $K_m$ (0.99 mM) of $PMD_{sc}$ toward MVAP are about 35-fold lower and 8-fold higher than the reported $k_{cat}$ (4.9 s$^{-1}$) and $K_m$ (123 µM) toward the native substrate (MVAPP), respectively (Krepkiy and Miziorko, 2004).

With a confirmation of promiscuous PMD$_{sc}$ activity for MVAP, a new IPP-bypass pathway (pathway II in FIG. 12) is constructed by expressing AtoB, HMGS, HMGR, MK, and PMD$_{sc}$ in E. coli (strain ARK2a, Table 2). Strain ARK2a produces 474.7 mg/L of isopentenol, a 558-fold improvement over the strain with pathway I (strain ARK3a). This new strain (strain ARK2a) achieves about 62.4% of the titer of the original isopentenol pathway (pathway O with strain ARK1a). It is noteworthy that IPP-bypass pathway II produces isopentenol even without over-expressing any additional phosphatase that would hydrolyze the phosphate group in IP.

3.4. Identification of Endogenous Phosphatase for IP

Figure 14A:
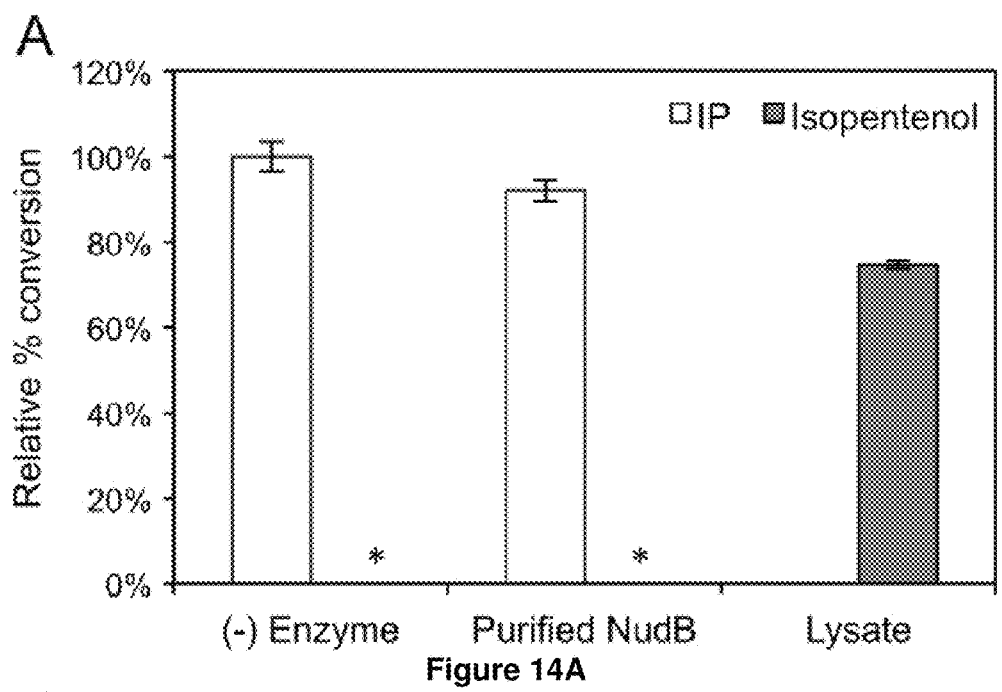
FIG. 14A. Hydrolysis of IP and IPP by purified NudB or E. coli cell lysates. IP hydrolysis. IP was hydrolyzed to isopentenol by E. coli cell lysates while isopentenol was not detected (*) from other two reactions with or without purified NudB.
Figure 14B:
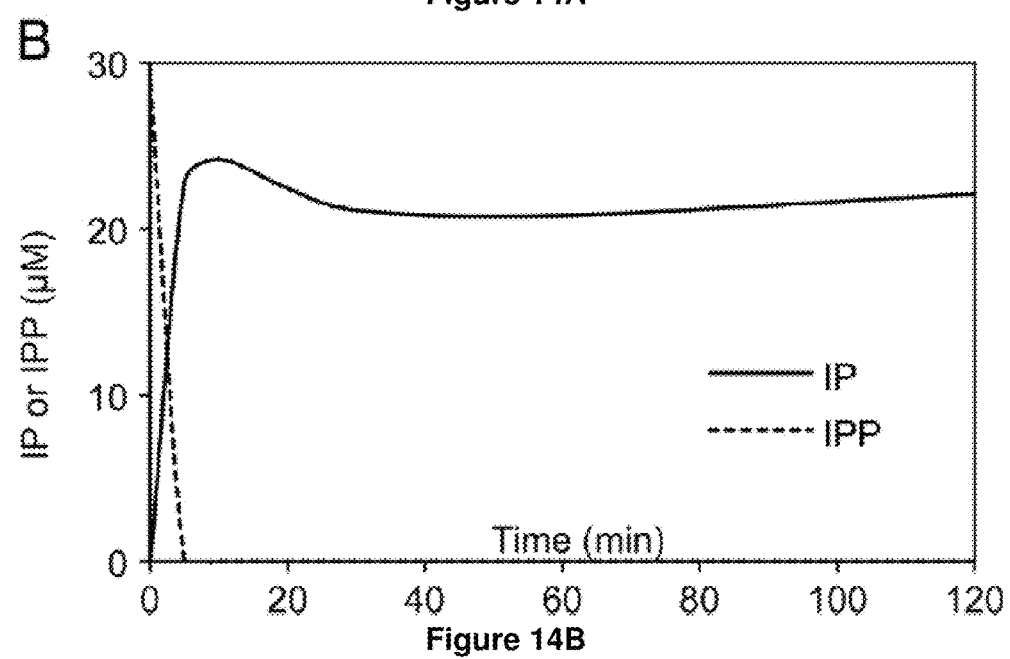
FIG. 14B. Hydrolysis of IP and IPP by purified NudB or E. coli cell lysates. Profile of IP and IPP concentrations in in vitro hydrolysis reactions of IPP by purified NudB.
Figure 15A:
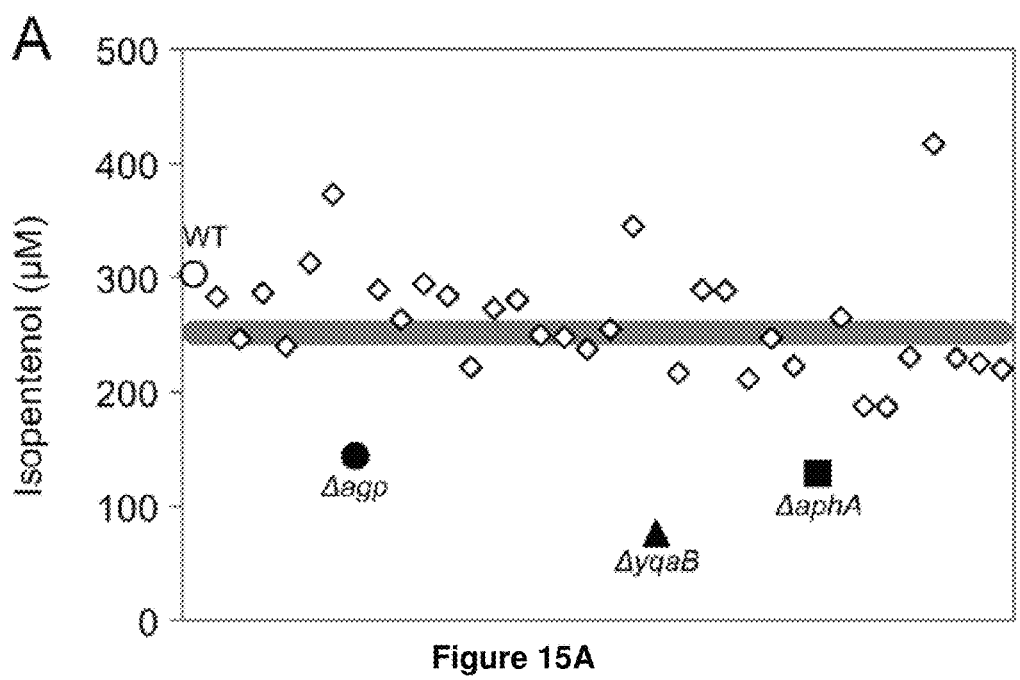
FIG. 15A. Identification of endogenous phosphatases for IP. Isopentenol concentration (μM) in the cell lysates of monophosphatase mutants. A total of 36 mutants (diamonds)—including Δagp (solid circle), ΔyqaB (solid triangle), ΔaphA (solid square) mutants and wild type BW25113 (open circle)—are screened. The gray line represents the average (251.9 μM) of isopentenol concentrations detected from all mutants.
Figure 15B:
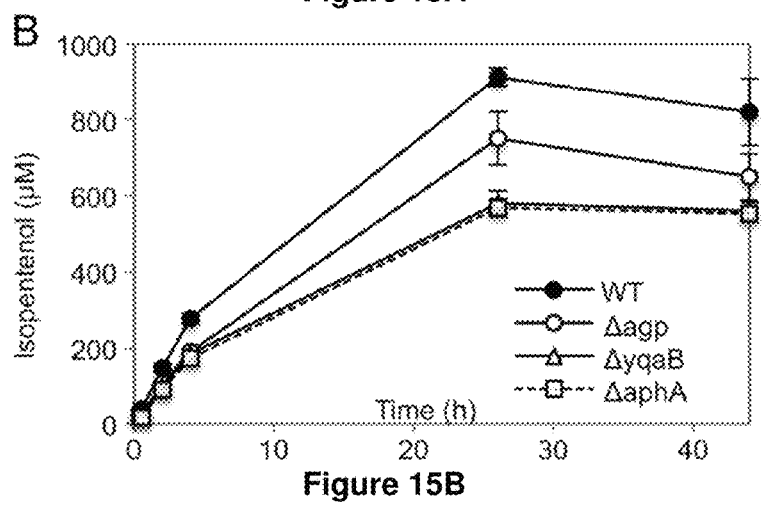
FIG. 15B. Identification of endogenous phosphatases for IP. Isopentenol converted from 1 mM IP by cell lysates of wild type (BW25113, solid circle), Δagp (open circle), ΔyqaB (open triangle) and ΔaphA (open square) mutants.
Figure 15C:
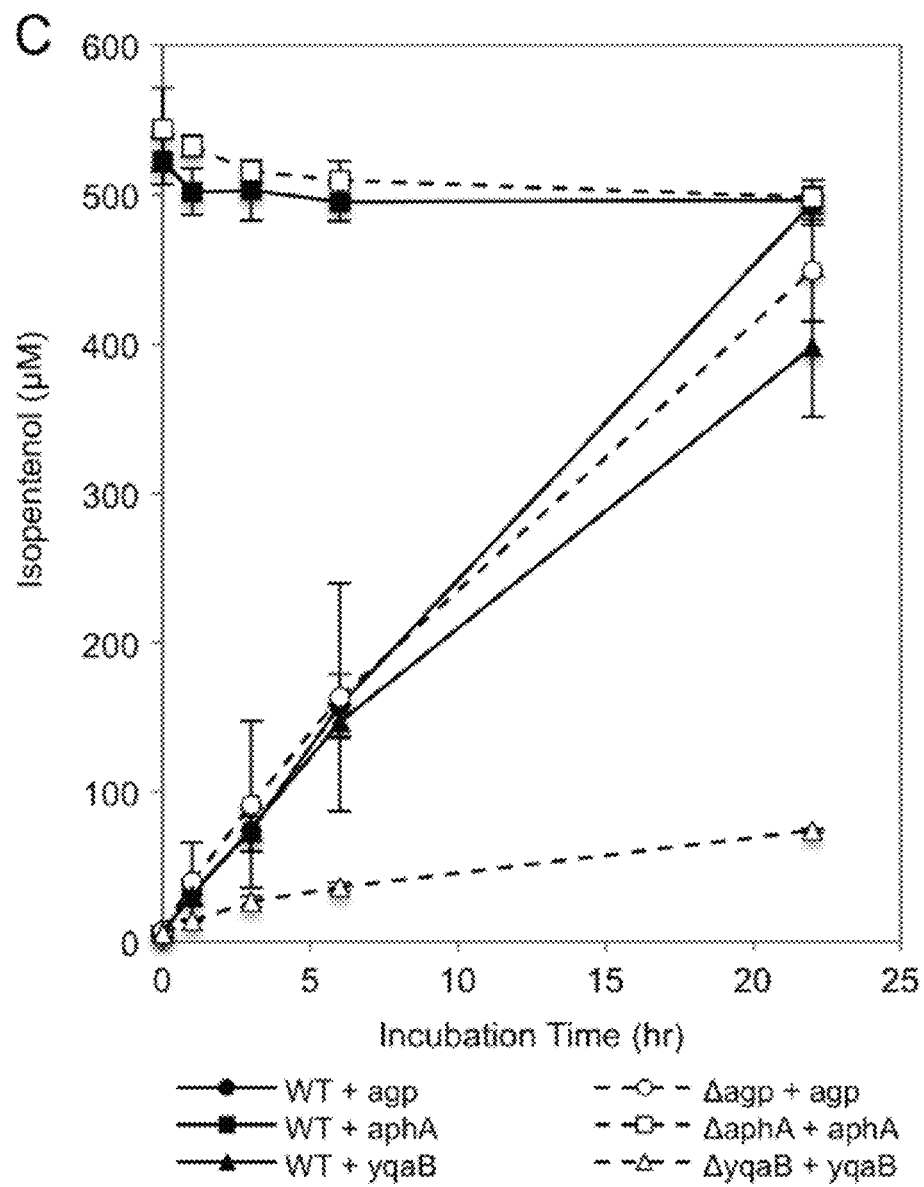
FIG. 15C. Identification of endogenous phosphatases for IP. Isopentenol converted from 500 μM IP by cell lysates of wild type (solid lines) or each mutant (dotted lines) with overexpression of the corresponding gene: agp (circle), yqaB (triangle) and aphA (square).
Figure 16:
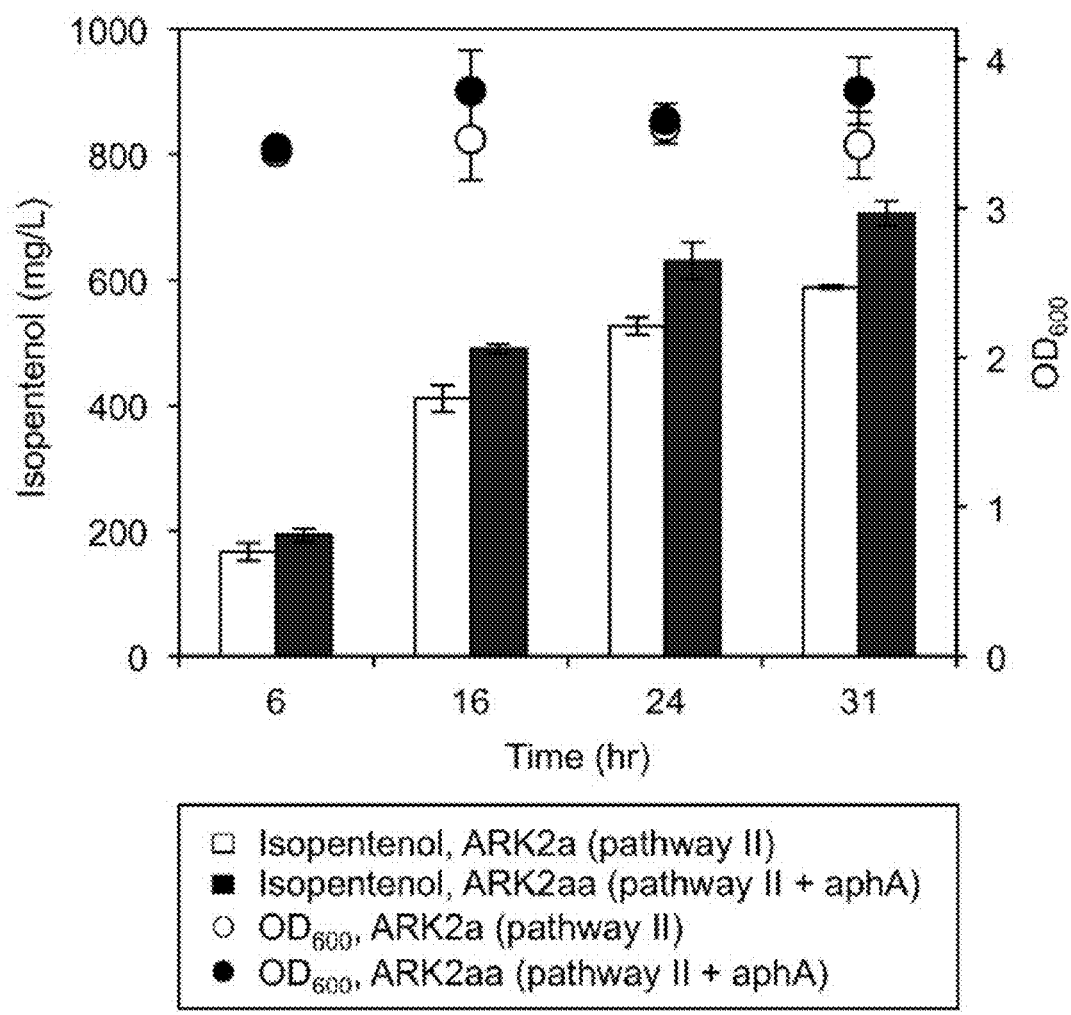
FIG. 16. Effect of aphA expression on isopentenol production in pathway II. Isopentenol from pathway II with (dark gray bar) or without aphA expression (white bar). Optical density of cell cultures at 600 nm ($OD_{600}$) for pathway II with (solid circle) or without aphA expression (open circle).

The successful production of isopentenol via IPP-bypass pathway II suggests that endogenous E. coli phosphatases are capable of hydrolyzing IP to isopentenol. Initially, it is hypothesized that IP may be hydrolyzed by promiscuous activities of Nudix hydrolases such as NudB in E. coli or an E. coli homolog of B. subtilis NudF, both of which were previously used to convert IPP to isopentenol (Chou and Keasling, 2012 and Withers et al., 2007). In the original IPP-dependent isopentenol pathway, the expression of NudB or NudF is essential for isopentenol production from IPP, and in vitro kinetic experiments of NudB showed that IPP was hydrolyzed by the enzyme (Chou and Keasling, 2012). However, the previous assay was based on the detection of the monophosphate formation without analyzing the final product by LCMS or GCMS, and it was not determined whether NudB hydrolyzes IPP by two consecutive hydrolysis reactions of two monophosphates or by a single hydrolysis reaction of a diphosphate group. It is hypothesized that if NudB hydrolyzes IPP via the former fashion (i.e. two consecutive hydrolyses), both IP (intermediate) and isopentenol would be detected from an in vitro assay containing purified NudB and IPP. Interestingly, an in vitro assay of purified NudB with IPP produces only IP—no isopentenol is detected even after an extended incubation of 16 hours (FIG. 14A). Similarly, purified NudB can hydrolyze DMAPP to DMAP, but the final hydrolysis product, 3-methyl-2-buten-1-ol, is not detected. In addition to NudB, NudF of B. subtilis, which was identified as a IPP hydrolase in a previous study (Withers et al., 2007), is also found to hydrolyze IPP to IP, but not to isopentenol. On the other hand, it is confirmed in vitro that crude cell lysates of E. coli do hydrolyze IP to isopentenol (FIG. 14B). This result suggests that in the original isopentenol pathway, NudB hydrolyzes IPP to IP, but the following hydrolysis of IP to isopentenol is catalyzed by unknown endogenous phosphatase(s) in E. coli.

3.5. PMD Engineering for Improved Activity Toward Mevalonate Monophosphate

To engineer the active site of PMD$_{sc}$ for the non-native substrate MVAP, amino acid residues in PMD putatively responsible for binding the native substrate (MVAPP) are first identified. Since the only X-ray crystal structure of PMD$_{sc}$ was solved without a bound substrate (Bonanno et al., 2001), the coordinates of MVAPP in the active site of PMD$_{sc}$ are predicted by aligning the crystal structure of PMD$_{sc}$ (PDB#: 1FI4) to that of the homologous PMD enzyme from S. epidermis (PMD$_{se}$, PDB#: 4DPT). Crystal structures of PMD$_{se}$ are solved with two substrate analogs: adenosine 5-[γ-thio]triphosphate (ATPγS) and 6-fluoromevalonate 5-diphosphate (FMVAPP) (Barta et al., 2012). Alignment of PMD$_{sc}$ and PMD$_{se}$ amino acid sequences shows 50% similarity by BLAST search and reveals conserved residues for catalysis and substrate binding. However, in vivo isopentenol production with IPP-bypass pathway II and PMD$_{se}$ (strain ARK4) is significantly reduced relative to PMD$_{sc}$ (11.3 mg/L vs 474.7 mg/L after 24 h), suggesting that the activity of PMD$_{se}$ toward MVAP could be much lower than that of PMD$_{sc}$. The $k_{cat}/K_m$ ratios of PMD$_{sc}$ and PMD$_{se}$ are 4.0×10$^4$ s$^{-1}$ M$^{-1}$ (Krepkiy and Miziorko, 2004) and 6.5×10$^5$ s$^{-1}$ M$^{-1}$ (Barta et al., 2012), respectively, which indicates higher substrate specificity of PMD$_{se}$ for MVAPP. Increased substrate specificity in PMD$_{se}$ can be attributed to the positively charged arginine at residue 193 (R193) (Barta et al., 2012). R193 of PMD$_{se}$ is located within hydrogen bonding distance of the β-phosphate moiety of MVAPP and stabilizes the binding of MVAPP to the enzyme. On the other hand, PMD$_{sc}$ has a neutral threonine residue in the homologous position (T209) instead of the positively charged arginine, and this perhaps allows the promiscuity of PMD$_{sc}$ towards the less negatively charged MVAP.

After the bypass pathway II with PMD$_{sc}$ is engineered, an archaeal MVAP-specific decarboxylase is identified in Haloferax volcanii (PMD$_{hv}$) with much better kinetics for MVAP ($K_m$ of 0.159 mM and $k_{cat}$ of 3.5 s$^{-1}$ for MVAP; and no activity toward MVAPP) (Vannice et al., 2014). Unlike the conventional MVA pathway that supplies IPP via decarboxylation of MVAPP, the archaeal MVA pathway produces IPP via phosphorylation of IP, which is produced by decarboxylation reaction of MVAP similar to our bypass pathway II. Therefore, PMD$_{hv}$ is expected to be a natural decarboxylase that can convert MVAP to IP in the IPP-bypass pathway II. Surprisingly, however, no isopentenol production is detected when four pathway genes in the bypass pathway II (AtoB, HMGS, HMGR and MK) are expressed in vivo along with PMD$_{hv}$ (strain ARK5; data not shown). An ATP-NADH coupled assay is also performed in vitro to detect the activity of PMD$_{hv}$ toward MVAP, but no ATP hydrolysis activity is observed either. In the previous work where PMD$_{hv}$ kinetics were determined, PMD$_{hv}$ is overexpressed in its native host, H. volcanii, at 42° C. in salt-rich Hv-YPC media (containing 144 g of NaCl, 21 g of MgSO$_4$.7H$_2$O, 18 g of MgCl$_2$.6H$_2$O and 4.2 g of KCl) (Vannice et al., 2014). Given that optimal growth temperatures and salt concentration in media of H. volcanii are different from those for E. coli, PMD$_{hv}$ can have been expressed but inactive in E. coli. Nonetheless, it is noteworthy that four residues from PMD$_{sc}$ that interact with β-phosphates of MVAPP are missing in PMD$_{hv}$ between threonine 186 (T186) and glutamate 187 (E187) (Vannice et al., 2014). In other homologous PMD sequences from species with conventional MVA pathways, these missing residues are rich in serine and arginine, which facilitates interaction with the phosphoryl moieties of MVAPP and ATP. Therefore, analysis of residues near β-phosphate of MVAPP in three PMDs suggested that the activity of PMD$_{sc}$ toward MVAP can be improved by re-designing the local electrostatic environment around the β-phosphate of MVAPP.

Figure 6A:
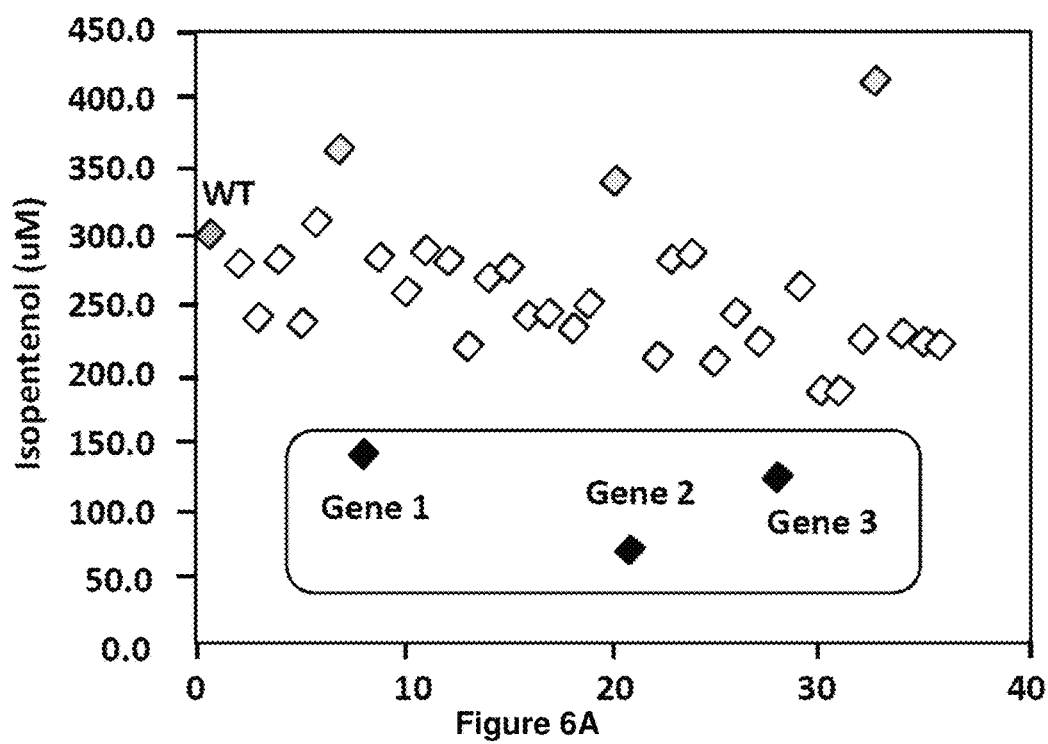
FIG. 6A. Phosphatase screening. The cell lysis of individual phosphatase knock-out strains from Keio collection was added to reaction mixture with IP, and isopentenol production was measured. Three knock-out strains (Gene 1, Gene 2, and Gene 3) were identified as lower producing strains.
Figure 6B:
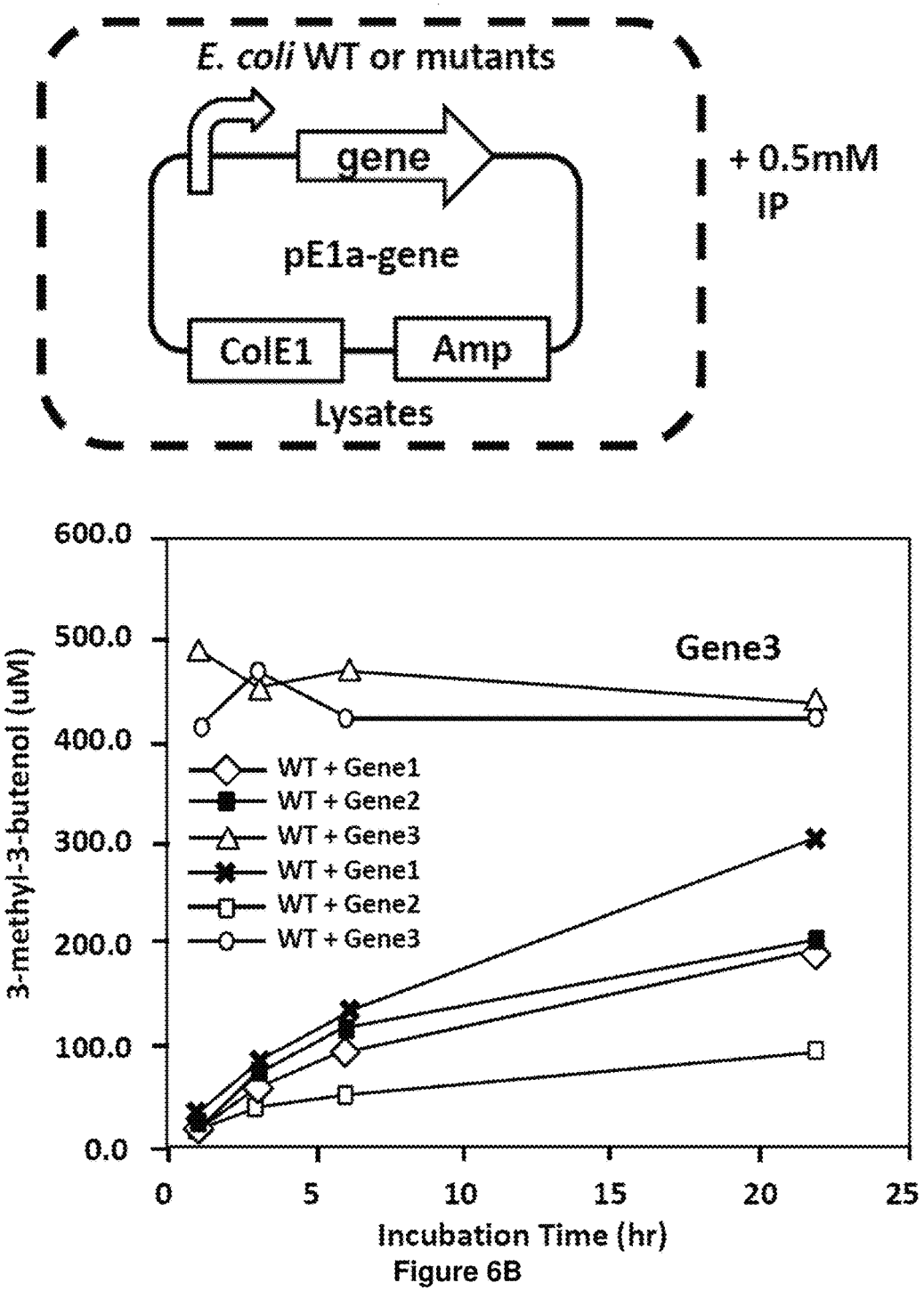
FIG. 6B. In vitro verification of three phosphatases for activity toward IP. Both wild type BW251132 strain and three Keio strains were transformed with each of three phosphatase genes, and each cell lysate was added to the assay mixture with 0.5 mM IP. Isopentenol production was monitored over one day and 4 time points were taken from each sample.
Figure 7:
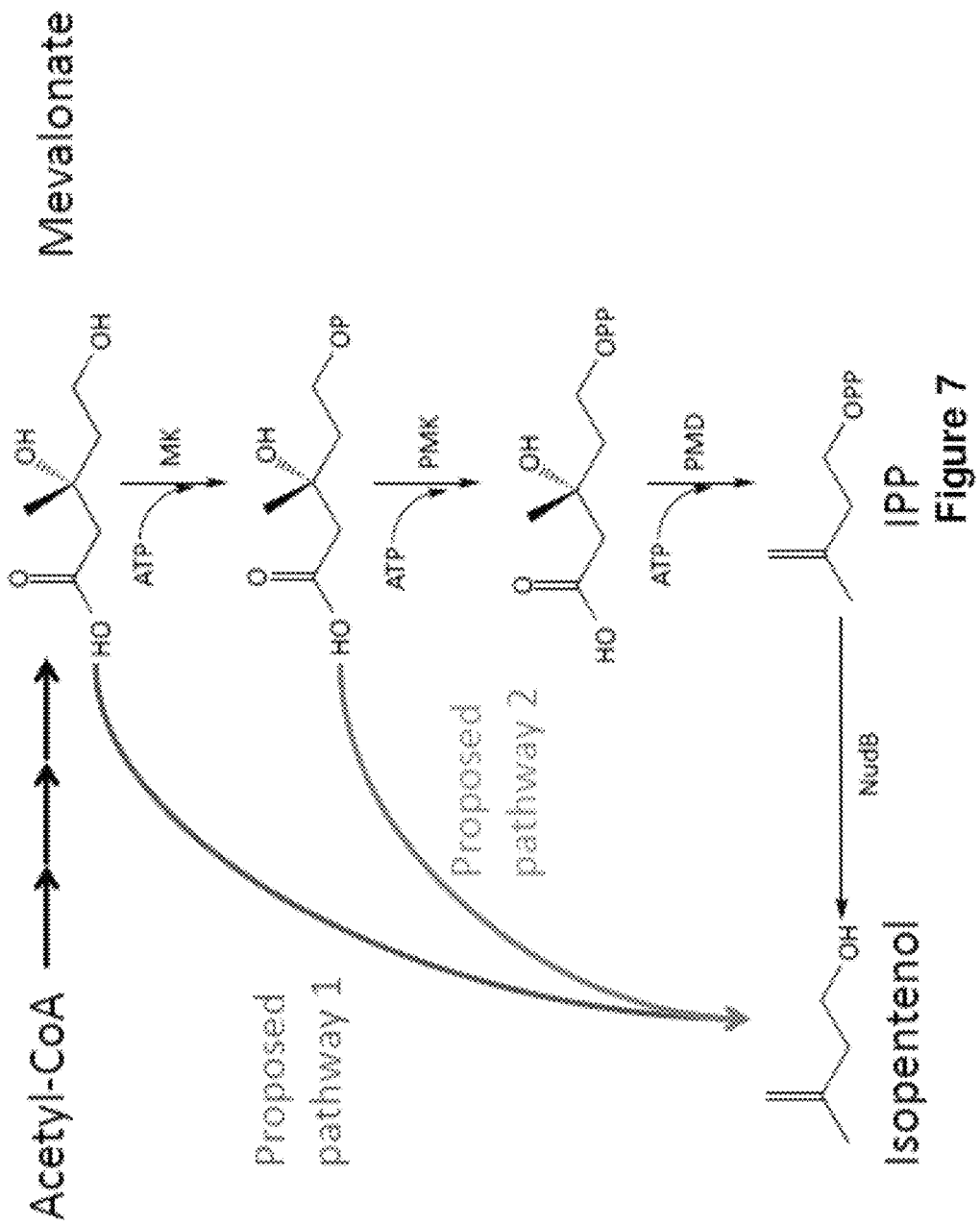
FIG. 7. Pathway from mevalonate to isopentenol.
Figure 8:
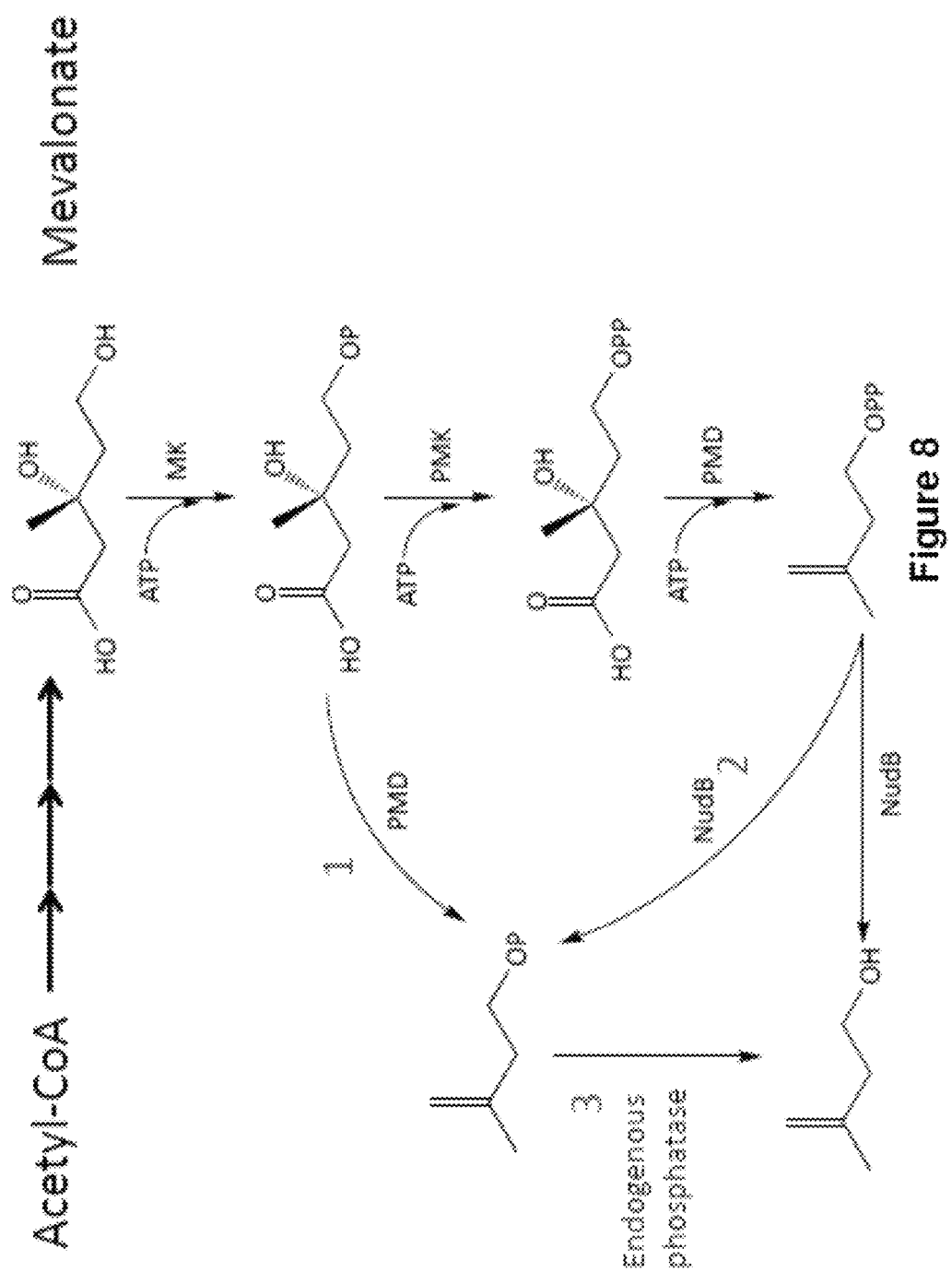
FIG. 8. Promiscuous reactions of the isopentenol pathway.
Figure 9:
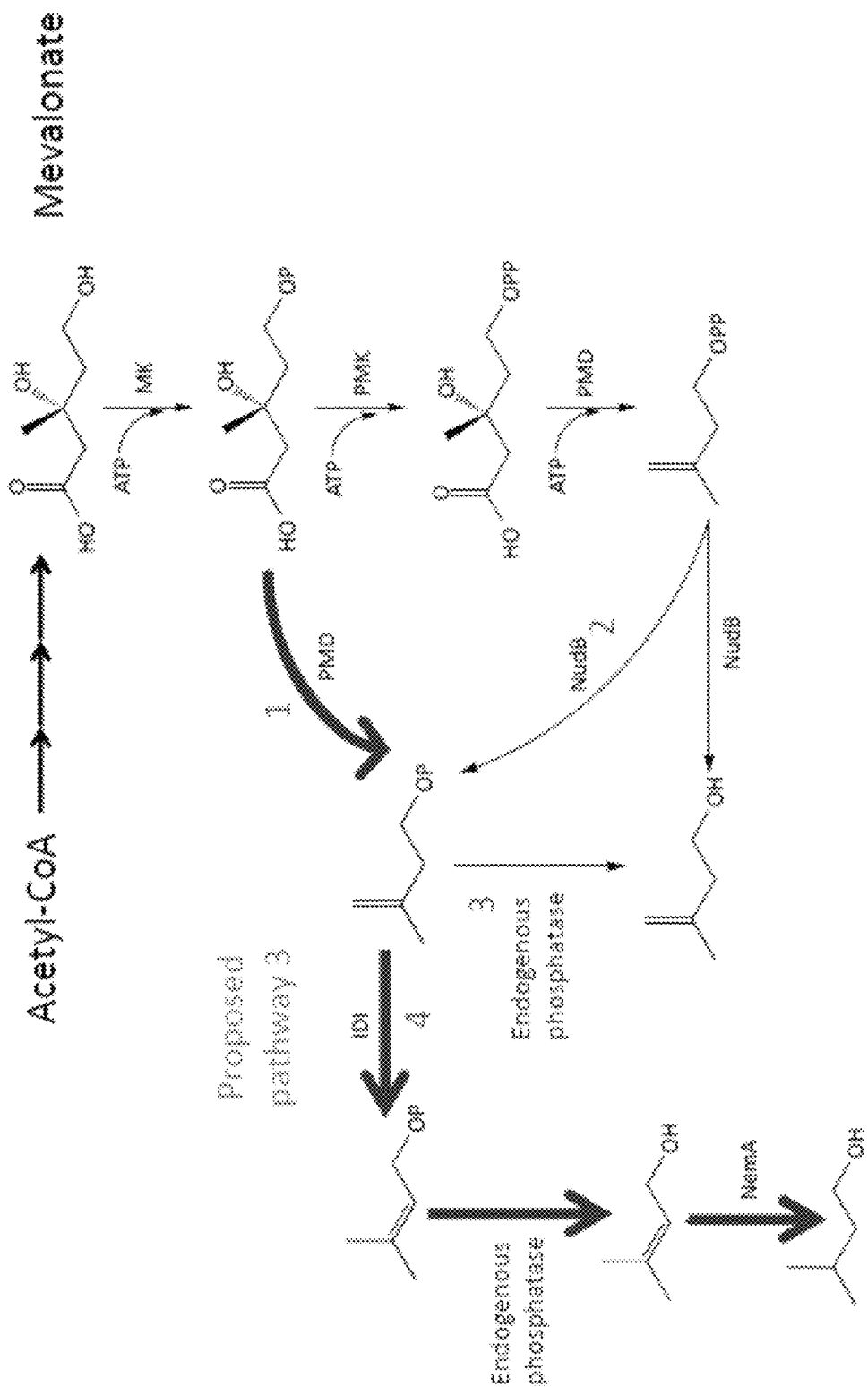
FIG. 9. Pathway extended to isopentanol.
Figure 10:
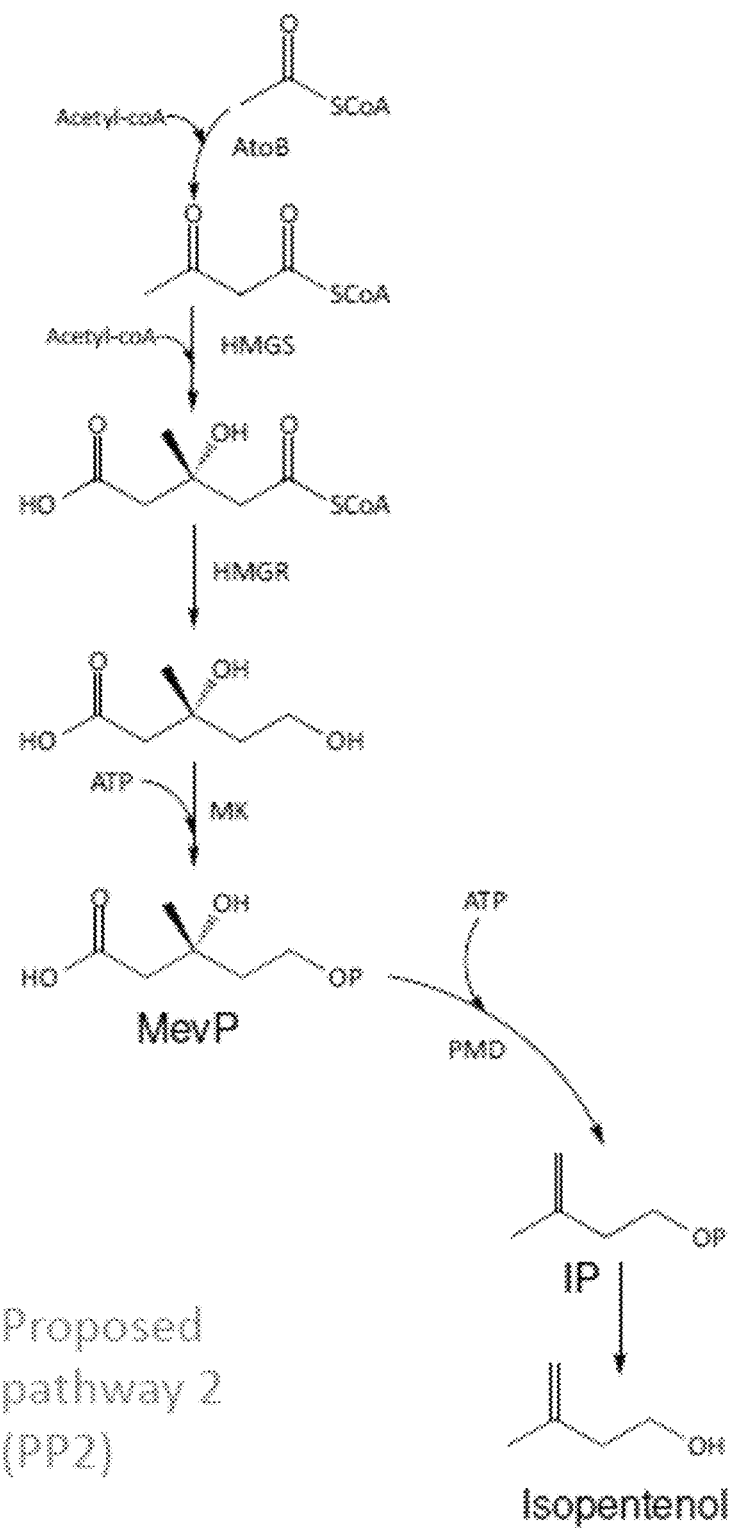
FIG. 10. Isopentenol production by PP2. The modified pathway which lacks PMK and NudB is tested under aerobic condition to determine whether isopentenol is produced. The modified pathway produced similar titer of isopentenol to that of the original pathway with PMK and NudB.
Figure 11:
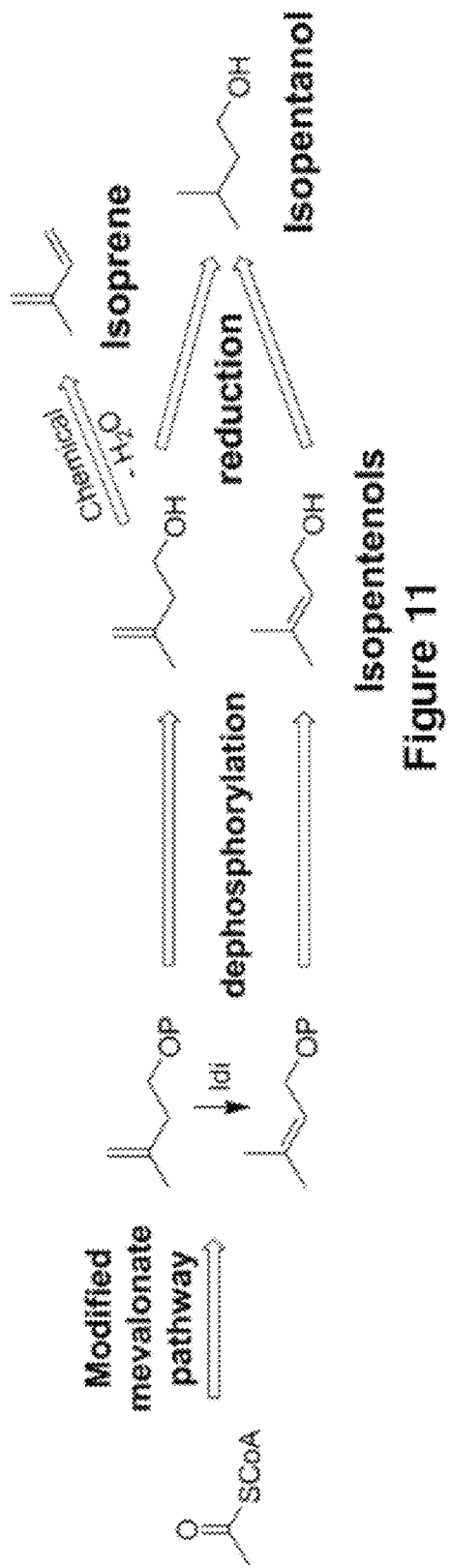
FIG. 11. Application of a new pathway to produce isopentenol.

Based on structural analysis of these three PMDs (PMD$_{sc}$, PMD$_{se}$, and PMD$_{hv}$), four residues (K22, S155, S208 and T209) of PMD$_{sc}$ adjacent to the β-phosphate of the MVAPP are selected for engineering. While the original substrate MVAPP has a net charge of −4, two alternative substrates, MVAP and MVA, have a net charge of −2 and 0, respectively. To compensate for this reduced negative charge, two serine residues (S155 and S208) are mutated to negatively charged glutamate (E), and the other two residues near the phosphate moiety (K22 and T209) are mutated to neutral methionine (M) and negatively charged aspartate (D), respectively. In addition, two more mutants, R74H and I145F (FIG. 17A) are constructed, which were previously shown to increase activity of $PMD_{sc}$ in the similar decarboxylation reaction for 3-hydroxy-3-methylbutyrate (3-HMB) to produce isobutene (Gogerty and Bobik, 2010). In vitro assay reactions using cell lysates of two serine-to-glutamate mutations (S155E and S208E) do not produce detectable amount of product, which suggests that these two mutations significantly reduce the activity of $PMD_{sc}$ toward MVAP unlike the other mutants (data not shown). The K22M mutation increased $K_m$ and decreased $k_{cat}$, but the kinetic parameters of the T209D mutant are similar to those of the wild type (Table 3, FIG. 17B). Interestingly, the specificity of $PMD_{sc}$ toward MVAP ($k_{cat}/K_m$) with R74H or I145F mutation is 220% and 147% of that of wild type, respectively. Although R74 and I145 are located near the active site, it is unlikely that these residues interact directly with substrates: distances from the α-phosphate group of MVAPP are 12.5 Å and 15.0 Å, respectively (FIG. 6A). Therefore, the improved activity of the R74H and I145F mutants toward MVAP and 3-HMB suggests that these two mutations change the conformation of the active site to accommodate less negatively charged substrates. Although R74H and I145F increase activity for MVAP and 3-HMB, these two mutants do not show detectable hydrolysis activity on MVA.

of PMD toward MVAP, this result provides a clear opportunity to improve IPP-bypass pathway II for isopentenol production.

3.6. Effect of MVA Levels on Isopentenol Production in the IPP-Bypass Pathway II IPP-bypass MVA pathways are engineered for isopentenol production and show that pathway II can be improved by facilitating two limiting reactions: hydrolysis of IP and decarboxylation of MVAP to IP. Next, the "top" portion of the MVA pathway is targeted with engineering that would modulate pathway flux to MVA and tested how this variation affects isopentenol production in IPP-bypass pathway II. Previously, heterologous MVA pathways are constructed and tested with various combinations of HMGS and HMGR, and different pairs of HMGS-HMGR result in different levels of MVA and final isoprenoid titers (George et al., 2014, Pfleger et al., 2006, Pitera et al., 2007 and Ma et al., 2011). The MVA level is reported to affect MK activity by substrate inhibition (Ma et al., 2011), and therefore, optimizing MVA flux has been one approach to improve titers of isoprenoid products.

To evaluate the effects of MVA concentration in IPP-bypass pathway II, the original and the modified pathways are reconstructed with four different pairs of HMGS and HMGR in the "top" portion of the pathway (FIG. 12): non-codon optimized original sequences from S. cerevisiae genes (MevTo), E. coli-codon optimized sequences of S.

TABLE 3

Kinetic parameters of PMD wild type, $PMD_{sc}$ mutants, $PMD_{se}$, $PMD_{hv}$ from other literature.

| Name | | $K_m$ (mM) | $k_{cat}$ (s$^{-1}$) | $k_{cat}/K_m$ (s$^{-1}$ M$^{-1}$) | % of WT | Substrate | Reference |
|---|---|---|---|---|---|---|---|
| $PMD_{sc}$ | WT | 0.99 | 0.14 | $1.4 \times 10^2$ | 100% | | |
| | R74H | 0.77 | 0.23 | $3.0 \times 10^2$ | 220% | | |
| | K22M | 2.47 | 0.09 | $3.5 \times 10^1$ | 25% | MVAP | This study |
| | T209D | 0.99 | 0.13 | $1.3 \times 10^2$ | 98% | | |
| | I145F | 1.36 | 0.28 | $2.0 \times 10^2$ | 147% | | |
| $PMD_{hv}$ | | 0.159 | 3.5 | $2.2 \times 10^4$ | | MVAP | (Vannice et al., 2014) |
| $PMD_{se}$ | | 0.009 | 5.9 | $6.5 \times 10^5$ | | MVAPP | (Barta et al., 2012) |
| $PMD_{sc}$ | | 0.123 | 5.4 | $4.0 \times 10^4$ | | MVAPP | (Krepkiy and Miziorko, 2004) |

Figure 17C:
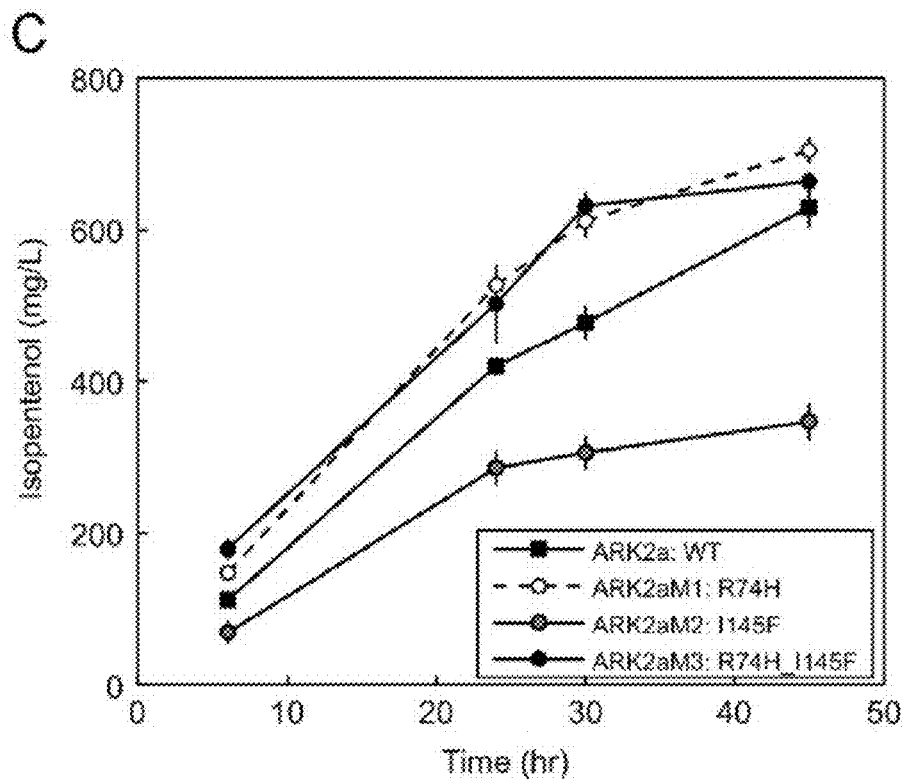
FIG. 17C. Effect of mutations on isopentenol production with IPP-bypass pathway II. Isopentenol production from strains with pathway II containing different PMD mutants including wild type (WT, black square), R74H (open circle), I145F (gray circle) and R74H/I145F double mutants (black circle).

After identifying two mutations in $PMD_{sc}$ that improve activity toward MVAP, E. coli strains overexpressing four enzymes (AtoB, HMGS, HMGR, MK) are prepared along with one of three different PMD mutants including R74H (stain ARK2a$_{M1}$), I145F (strain ARK2a$_{M2}$), or the double mutant (strain ARK2a$_{M3}$) to see whether improved specificity for MVAP would increase isopentenol production in IPP-bypass pathway II. As shown in FIG. 17C, R74H (strain ARK2a$_{M1}$) result in significantly improved productivity (20.4 mg/L/hr) over wild type (15.9 mg/L/hr) through 30 hours of batch fermentation. The I145F mutation (strain ARK2a$_{M2}$), however, reduces isopentenol titer and productivity in vivo even though this mutation improves in vitro enzyme activity (Table 3). Interestingly, when these two mutations are combined (strain ARK 2a$_{M3}$), the titer and productivity are recovered to the comparable level to those of R74H, which suggests that R74H mutation is dominant over the I145F mutation.

Successful identification of PMD mutants that improve or significantly reduce isopentenol titer and productivity supports the hypothesis that the promiscuous activity of PMD toward MVAP is the current bottleneck of the IPP-bypass pathway II. Given the huge engineering space to explore various mutations that can potentially improve the activity cerevisiae genes (MevTco), HMGS and HMGR of Staphylococcus aureus (MTSA), and those of Delftia acidovorans (MTDA).

Figure 18:
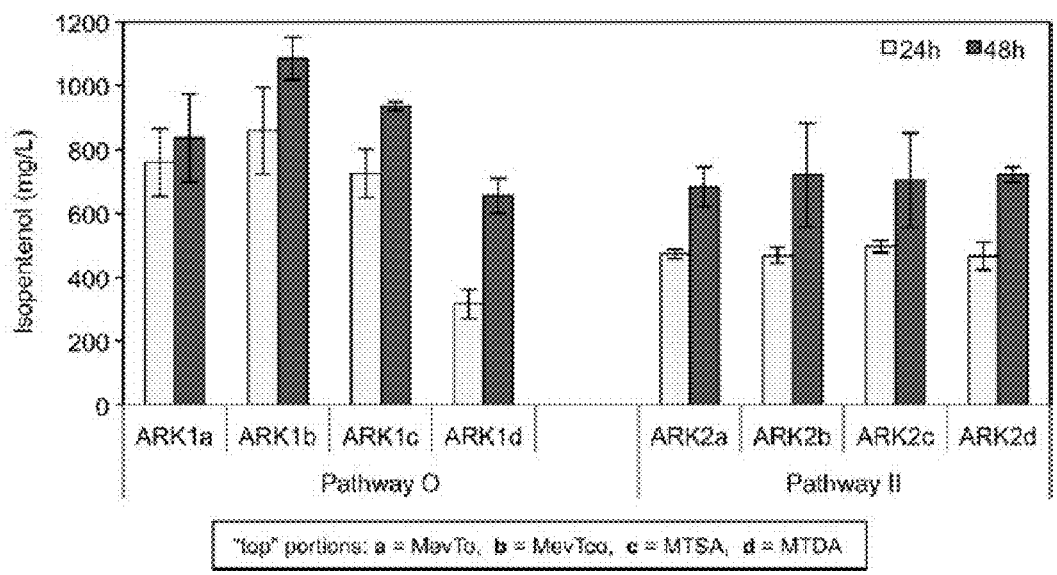
FIG. 18. Effect of different "top" portions on isopentenol production in *E. coli* with pathway O or with pathway II. Four different "top" portions have different HMGS and HMGR sequences, which are original sequences from. *S. cerevisiae* (MevTo), codon-optimized sequences of *S. cerevisiae* (MevTco), sequences from *S. aureus* (MTSA) and sequences from *D. acidovorans* (MTDA). Isopentenol production was measured at 24 hours (white dotted bar) and at 48 h (gray bars).

In accordance with the previous reports, the original IPP-dependent isopentenol pathways show different isopentenol titers depending on which pairs of HMGS and HMGR are used (FIG. 18). Analysis of intracellular metabolites confirm that expression of different pairs of HMGS and HMGR indeed result in various intracellular MVA concentrations in strains with both pathway O and pathway II. Intriguingly, isopentenol titers from the strains containing IPP-bypass pathway II do not change much when the pairs of HMGR and HMGS are changed (FIG. 18), and similar levels of IP are also observed in the strains with pathway II. This "insensitivity" of the isopentenol titer to various "top" portions and a similar level of IP in pathway II strains suggests that the determining factor of isopentenol production in pathway II can be the PMD activity toward MVAP rather than upstream pathway efficiency.

In addition, metabolite analysis shows that strains with pathway O or pathway II accumulate significantly high levels of IPP or MVAP, respectively, regardless of intracellular MVA concentrations. Interestingly, MVAP is accumulated to considerably higher concentrations than that of IPP (100-200 mM for MVAP vs 30-60 mM for IPP) without any significant toxicity, which is consistent with the previous report that MVAP is not inhibitory to cell growth (Martin et al., 2003).

3.7. Relief of IPP-Toxicity in the Bypass Pathway II

Previous studies showed that the performance of the original MVA pathway was sensitive to MK expression levels: low MK expression resulted in attenuated flux to IPP and isopentenol, but high levels led IPP accumulation and resulted in growth inhibition (George et al., 2014 and George et al., 2015). Interestingly, growth is restored when NudB is overexpressed in IPP-accumulating strain to relieve IPP-toxicity. In Example 3, it is demonstrated that NudB hydrolyzes IPP to IP, but not further to isopentenol (FIG. 14), suggesting that IPP has more detrimental effects on growth than does IP.

Figure 19A:
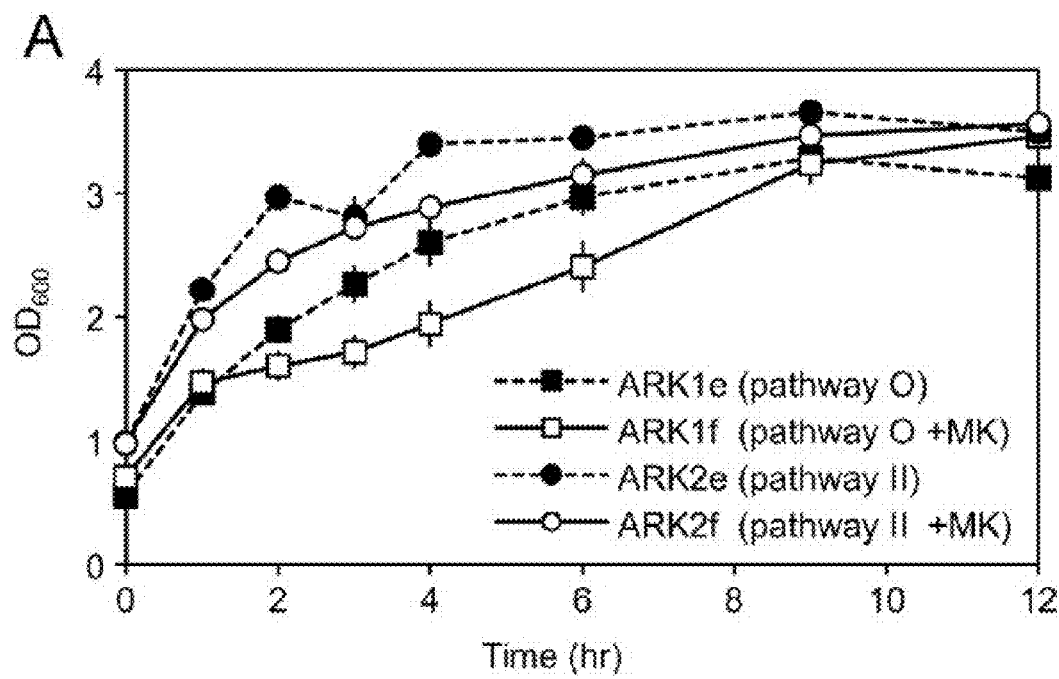
FIG. 19A. IPP toxicity in Pathway O. Growth of four strains containing Pathway O without (black, square) or with expression of additional MK (white square); Pathway II without (black, circle) or with expression of additional MK (white circle).
Figure 19B:
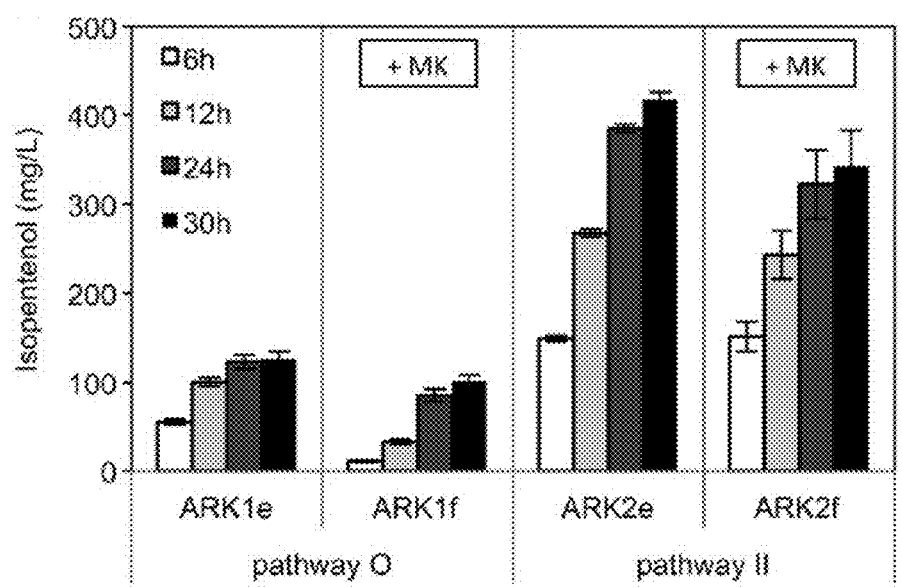
FIG. 19B. IPP toxicity in Pathway O. Isopentenol production from four strains containing Pathway O without or with expression of additional MK; Pathway II without or with expression of additional MK.

Since the bypass pathway II does not produce IPP, it is hypothesized that the pathway would be insensitive to changes in MK expression and free from related toxicity. To compare growth and isopentenol production in the original and IPP-bypass pathway (pathway O and pathway II) under IPP- or IP-accumulating conditions, respectively, two modifications are made to the strains ARK1a and ARK2a. First, to achieve a moderate level of MK expression in the control strains, the promoter previous added for MK overexpression is removed in the medium copy plasmids JBEI-12056 and JBEI-9310. With this engineering, MK expresses at a moderate level as the forth enzyme in the operon containing three enzymes for the top portion of the MVA pathway, and it results strains ARK1e (harboring JBEI-6818 and JBEI-6833) and ARK2e (harboring JBEI-12051 and JBEI-9314). Second, to achieve very high MK expression level, an additional copy of MK is added to the high copy plasmids, JBEI-6833 and JBEI-9314, resulting ARK1f and ARK2f, respectively. Confirming the previous results (George et al., 2014), balancing flux in the upstream pathway is critical for growth and isopentenol production (FIG. 19). Growth and isopentenol production of ARK1f is significantly reduced showing sensitivity to expression levels of MK, but strains with pathway II is insensitive to down-regulation (ARK2f) or up-regulation (ARK2e) of MK, and free from burden of IPP accumulation (FIG. 19).

3.8. The Effect of Limited Aeration on Isopentenol Production Via IPP-Bypass Pathway After characterizing the IPP-bypass pathway II in E. coli (strain ARK2a), it is tested whether this pathway would have any advantage over the original pathway under ATP-limited conditions. In general, ATP is most efficiently supplied via oxidative phosphorylation with oxygen as a final electron acceptor. As a result, aeration has been an important operation in industrial-scale fermentation, especially when ATP-demanding isoprenoid biosynthetic pathways are exploited. However, the aeration cost is usually one of the largest portions (up to 26%) of the overall utility cost, and the cost would be on the order of $60 million per year in a plant that processes 2000 MT of dry biomass per day (Clark and Blanch, 1997). Moreover, oxygen mass transfer is limited in large-scale fermenters, and this potentially creates a local micro-aerobic or anaerobic environment during fermentation. Therefore, the development of fermentation processes with reduced aeration rates can significantly reduce production cost and improve process efficiency. With this goal in mind, the impact of reduced aeration on isopentenol production with pathways O and II is investigated, which require 3 ATPs and 2 ATPs, respectively, to produce one molecule of isopentenol. To provide different aeration rates, a 50-mL cell culture with an $OD_{600}$ of 0.6-0.7 is prepared, split into two 25-mL cell cultures in 250-mL flasks, and continued to incubate at 30° C. for induction (0.5 mM IPTG) at two different shaking speeds (30 rpm and 200 rpm).

Figure 20A:
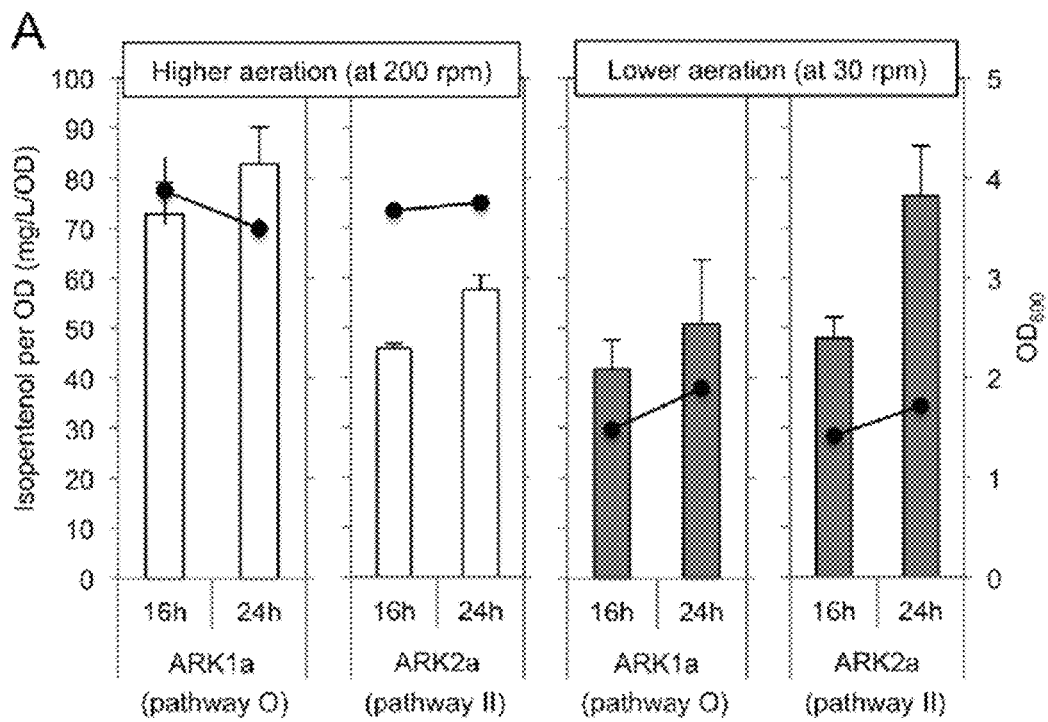
FIG. 20A. Effect of reduced aeration conditions on isopentenol production in *E. coli*. Isopentenol titers (per $OD_{600}$) of two strains with pathway O or with pathway II under higher (200 rpm) or lower (30 rpm) aeration conditions.
Figure 20B:
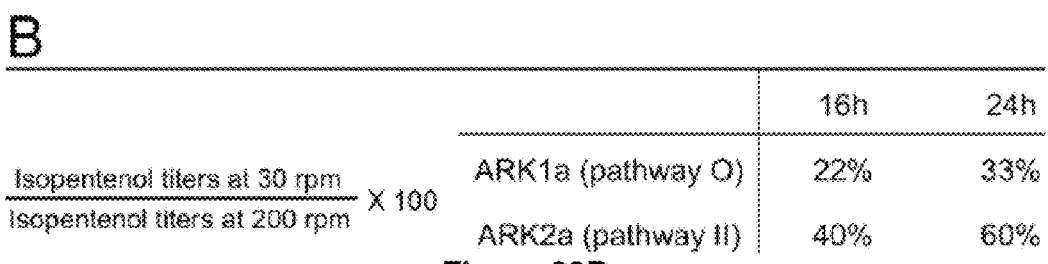
FIG. 20B. Effect of reduced aeration conditions on isopentenol production in *E. coli*. Relative isopentenol titers (total) of two pathways under lower aeration conditions (30 rpm) compared to those under higher aeration conditions (200 rpm).

FIG. 20A shows that the isopentenol titer of pathway O (strain ARK1a) is more significantly affected when aeration is limited by lowering the shaking speed from 200 rpm to 30 rpm. With a reduced aeration, strain ARK1a produced only 22% of the initial titer at 200 rpm after 16 h-fermentation (FIG. 20B). The bypass pathway II (strain ARK2a), however, produces 40% at 16 h and up to 60% of the titers under the higher aeration conditions at 24 h. It is noteworthy that the $OD_{600}$ of strain ARK1a is higher than that of strain ARK2a under poor aeration condition (at 30 rpm). A better growth but significantly less isopentenol production of strain ARK1a suggests that the heterologous MVA pathway may compete for ATP with other essential cellular processes related to the growth, and when ATP supply is limited (i.e. under poor aeration conditions), strain ARK1a might reduce the carbon flux to the MVA pathway to reduce the energy usage for this ATP-consuming heterologous pathway. The strain with pathway II (strain ARK2a), however, produces a similar or even higher level of isopentenol under limited aeration conditions after 16 h or 24 h of fermentation, respectively (FIG. 20A). This result also suggests that the bypass pathway II would be more robust when aeration is limited, and a reduced ATP demand in strain ARK2a is possibly beneficial to the strain under oxygen-limited conditions. Therefore, more economic production of isopentenol could be feasible via the ATP-saving IPP-bypass pathway II by reducing aeration costs for large scale fermentation.

4. Conclusion

Isopentenol is a potential gasoline alternative and a precursor of commodity chemicals such as isoprene. Example 3 reports efforts to remove "IPP-dependency" of the original MVA pathway and to overcome limitations intrinsic to IPP accumulation and "unnecessary" consumption of ATPs for isopentenol production. By implementing two previously unidentified activities of $PMD_{sc}$ and AphA, it is demonstrated that considerable isopentenol titers could be achieved without producing IPP via the pathway II.

The IPP-bypass pathway II is shown to be a robust alternative to the original pathway (pathway O) for isopentenol production. This modified pathway is insensitive to both MVA level and MK expression level, and reduces the engineering burden to balance the upstream MVA pathway and IPP toxicity. Most significantly, the IPP-bypass pathway II is more competitive when aeration is limited, which would significantly lower operational costs for aeration in a large scale fermentation.

Finally, it is found that the promiscuous activity PMD is rate-limiting. The identification of PMD as the rate-limiting step in these bypass pathways provides clear engineering opportunities. Although a few PMD mutants with improved activity toward MVAP are constructed, more concerted efforts to engineer PMD promiscuity or identify homologous enzymes should yield additional increases in isopentenol yield and productivity. With further engineering, these bypass pathways will provide valuable platforms for the energetically-favored production of isopentenol, isoprene, and related $C_5$ compounds.

References Cited in Example 3

Anthony, J. R., Anthony, L. C., Nowroozi, F., Kwon, G., Newman, J. D., Keasling, J. D., 2009. Optimization of the mevalonate-based isoprenoid biosynthetic pathway in Escherichia coli for production of the anti-malarial drug precursor amorpha-4,11-diene. Metab. Eng. 11, 13-19.

Adolfsen, K. J., Brynildsen, M. P., 2015. Futile cycling increases sensitivity toward oxidative stress in Escherichia coli. Metab. Eng. 29, 26-35.

Alonso-Gutierrez, J., Chan, R., Batth, T. S., Adams, P. D., Keasling, J. D., Petzold, C. J., et al., 2013. Metabolic engineering of Escherichia coli for limonene and perillyl alcohol production. Metab. Eng. 19, 33-41.

Barta, M. L., McWhorter, W. J., Miziorko, H. M., Geisbrecht, B., 2012. Structural basis for nucleotide binding and reaction catalysis in mevalonate diphosphate decarboxylase. Biochemistry. 51, 5611-5621.

Baba, T., Ara, T., Hasegawa, M., Takai, Y., Okumura, Y., Baba, M., etal., 2006. Construction of Escherichia coli K-12 in-frame, single-gene knockout mutants: the Keio collection. Mol. Syst. Biol. 2,2006.0008.

Bonanno, J. B., Edo, C., Eswar, N., Pieper, U., Romanowski, M. J., Ilyin, V., etal., 2001. Structural genomics of enzymes involved in sterol/isoprenoidbiosynthesis. Proc. Natl. Acad. Sci. USA. 98, 12896-12901.

Chou, H. H., Keasling, J. D., 2012. Synthetic pathway for production of five-carbon alcohols from isopentenyl diphosphate. Appl. Environ. Microbiol. 78, 7849-7855.

Connor, M. R., Liao, J. C., 2008. Engineering of an Escherichia coli strain for the production of 3-methyl-1-butanol. Appl. Environ. Microbiol. 74, 5769-5775.

Connor, M. R., Cann, A. F., Liao, J. C., 2010. 3-Methyl-1-butanol production in Escherichia coli: Random mutagenesis and two-phase fermentation. Appl. Microbiol. Biotechnol. 86, 1155-1164.

Cohen, B. E., 2014. Functional linkage between genes that regulate osmotic stress responses and multidrug resistance transporters: challenges and opportunities for antibiotic discovery. Antimicrob. Agents Chemother. 58, 640-646.

Clark, D. S., Blanch, H. W., 1997. Biochemical Engineering, Second Edition CRC Press, accessed Dec. 8, 2015.

Dueber, J. E., Wu, G. C., Malmirchegini, G. R., Moon, T. S., Petzold, C. J., Ullal, A. V., etal., 2009. Synthetic protein scaffolds provide modular control over metabolic flux. Nat. Biotechnol. 27, 753-759.

Dahl, R. H., Zhang, F., Alonso-Gutierrez, J., Baidoo, E., Batth, T. S., Redding-Johanson, A. M., et al., 2013. Engineering dynamic pathway regulation using stress-response promoters. Nat. Biotechnol. 31, 1039-1046.

Degenhardt, J., Köllner, T. G., Gershenzon, J., 2009. Monoterpene and sesquiterpene synthases and the origin of terpene skeletal diversity in plants. Phytochemistry. 70, 1621-1637.

George, K. W., Chen, A., Jain, A., Batth, T. S., Baidoo, E., Wang, G., etal., 2014. Correlation analysis of targeted proteins and metabolites to assess and engineer microbial isopentenol production. Biotechnol. Bioeng. 111, 1648-1658.

George, K. W., Thompson, M. G., Kang, A., Baidoo, E., Wang, G., Chan, L. J. G., Petzold, C. J., Adams, P. D., Keasling, J. D., Lee, T. S., 2015. Metabolic engineering for the high-yield production of isoprenoid-based C5 alcohols in E. coli, Sci. Rep. 5, 11128, Gogerty, D. S., Bobik, T. A., 2010. Formation of isobutene from 3-hydroxy-3-methylbutyrate by diphosphomevalonate decarboxylase. Appl. Environ. Microbiol. 76, 8004-8010.

Hengge, R., 2008. The two-component network and the general stress sigma factor RpoS (sigmaS) in Escherichia coli. Adv. Exp. Med. Biol. 631, 40-53.

Kim, E. M., Eom, J. H., Um, Y., Kim, Y., Woo, H. M., 2015. Microbial Synthesis of Myrcene by Metabolically Engineered Escherichia coli. J. Agric. Food Chem. 63, 4606-4612.

Krepkiy, D., Miziorko, H. M., 2004. Identification of active site residues in mevalonate diphosphate decarboxylase: implications for a family of phosphotransferases. Protein Sci. 13, 1875-1881.

Liu, H., Sun, Y., Ramos, K. R. M., Nisola, G. M., Valdehuesa, K. N. G., Lee, W. K., et al., 2013. Combination of entner-doudoroff pathway with MEP increases isoprene production in engineered Escherichia coli. PLoS One 8,e83290.

Lee, T. S., Krupa, R. A., Zhang, F., Hajimorad, M., Holtz, W. J., Prasad, N., etal., 2011. BglBrick vectors and datasheets: a synthetic biology platform for gene expression. J. Biol. Eng. 5,12.

Martin, V. J. J., Pitera, D. J., Withers, S. T., Newman, J. D., Keasling, J. D., 2003. Engineering a mevalonate pathway in Escherichia coli for production of terpenoids. Nat. Biotechnol. 21, 796-802.

Ma, S. M., Garcia, D. E., Redding-Johanson, A. M., Friedland, G. D., Chan, R., Batth, T. S., et al., 2011. Optimization of a heterologous mevalonate pathway through the use of variant HMG-CoA reductases. Metab. Eng. 13, 588-597.

Peralta-Yahya, P. P., Zhang, F., delCardayre, S. B., Keasling, J. D., 2012. Microbial engineering for the production of advanced biofuels. Nature. 488, 320-328.

Pfleger, B. F., Pitera, D. J., Smolke, C. D., Keasling, J. D., 2006. Combinatorial engineering of intergenic regions in operons tunes expression of multiple genes. Nat. Biotechnol. 24, 1027-1032.

Pitera, D. J., Paddon, C. J., Newman, J. D., Keasling, J. D., 2007. Balancing a heterologous mevalonate pathway for improved isoprenoid production in Escherichia coli. Metab. Eng. 9, 193-207.

Redding-Johanson, A. M., Batth, T. S., Chan, R., Krupa, R., Szmidt, H. L., Adams, P. D., et al., 2011. Targeted proteomics for metabolic pathway optimization: Application to terpene production. Metab. Eng. 13, 194-203.

Sun, Y., Fukamachi, T., Saito, H., Kobayashi, H., 2011. ATP requirement for acidic resistance in Escherichia coli. J. Bacteriol. 193, 3072-3077.

Vannice, J. C., Skaff, D. A., Keightley, A., Addo, J. K., Wyckoff, G. J., Miziorko, H. M., 2014. Identification in Haloferax volcanii of phosphomevalonate decarboxylase and isopentenyl phosphate kinase as catalysts of the terminal enzyme reactions in an archaeal alternate mevalonate pathway. J. Bacteriol. 196, 1055-1063.

Withers, S. T., Gottlieb, S. S., Lieu, B., Newman, J. D., Keasling, J. D., 2007. Identification of isopentenol biosynthetic genes from Bacillus subtilis by a screening method based on isoprenoid precursor toxicity. Appl. Environ. Microbiol. 73, 6277-6283.

Wang, C., Yoon, S. H., Shah, A. A., Chung, Y. R., Kim, J. Y., Choi, E. S., etal., 2010. Farnesol production from Escherichia coli by harnessing the exogenous mevalonate pathway. Biotechnol. Bioeng. 107, 421-429.

Wagner, S., Klepsch, M. M., Schlegel, S., Appel, A., Draheim, R., Tarry, M., etal., 2008. Tuning Escherichia coli for membrane protein over expression. Proc. Natl. Acad. Sci. USA. 105, 14371-14376.

Zheng, Y., Liu, Q., Li, D., Qin, W., Yang, J., Zhang, H., etal., 2013. Metabolic engineering of Escherichia coli for high-specificity production of isoprenol and prenol as next generation of biofuels. Biotechnol. Biofuels 6,57.

Zhu, F., Zhong, X., Hu, M., Lu, L., Deng, Z., Liu, T., 2014. In vitro reconstitution of mevalonate pathway and targeted engineering of farnesene overproduction in *Escherichia coli*. Biotechnol. Bioeng. 111, 1396-1405.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell capable of producing isopentenol and/or 3-methyl-3-butenol, comprising (a) an increased expression of phosphomevalonate decarboxylase (PMD), wherein the PMD has an amino acid sequence having at least 90% identity with SEQ ID NO:1, and (i) amino acid residue at position 74 is histidine, (ii) amino acid residue at position 145 is phenylalanine, or (iii) amino acid residue at position 74 is histidine and amino acid residue at position 145 is phenylalanine, (b) an increased expression of a phosphatase capable of converting isopentenol into 3-methyl-3-butenol, (c) optionally the genetically modified host cell does not express, or has a decreased expression of one or more of dihydroneopterin triphosphate diphosphate (NudB), phosphomevalonate kinase (PMK), and/or PMD, and (d) optionally one or more further enzymes capable of converting isopentenol and/or 3-methyl-3-butenol into a third compound; wherein the host cell is a bacterial or fungal cell.

2. The genetically modified host cell of claim 1, wherein the decreased expression is a disruption of the promoter or knock out of the gene encoding NudB, PMK, and/or PMD.

3. The genetically modified host cell of claim 1, wherein the third compound is isoprene.

4. The genetically modified host cell of claim 1, further comprising an increased expression of one or more of acetyl-CoA acetyltransferase (AtoB), hydroxymethylglutaryl-CoA synthase (HMGS), hydroxymethylglutaryl-CoA reductase (HMGR), and/or mevalonate kinase (MK).

5. The genetically modified host cell of claim 1, wherein the PMD is encoded on a nucleotide sequence which is in nucleic acids which is transformed into the genetically modified host cell, or host cell prior to genetic modification.

6. The genetically modified host cell of claim 3, wherein one or more of the PMD, phosphatase, AtoB, HMGS, HMGR, and MK, are encoded on one or more nucleotide sequences which are in one or more nucleic acids which are transformed into the genetically modified host cell, or host cell prior to genetic modification.

7. A method for producing isopentenol and/or 3-methyl-3-butenol and/or the third compound, comprising: (a) providing a genetically modified host cell of claim 1, 2, or 3, (b) culturing the genetically modified host cell under a condition wherein phosphomevalonate decarboxylase (PMD) and/or phosphatase are expressed, and (c) optionally recovering the isopentenol and/or 3-methyl-3-butenol and/or the third compound.

8. The method of claim 7, wherein the (b) culturing step further comprises expressing acetyl-CoA acetyltransferase (AtoB), hydroxymethylglutaryl-CoA synthase (HMGS), hydroxymethylglutaryl-CoA reductase (HMGR), and/or mevalonate kinase (MK).

9. The method of claim 7, wherein the (b) culturing step is under an anaerobic or microaerobic condition.

10. The method of claim 8, wherein the (b) culturing step is under an anaerobic or microaerobic condition.

11. The genetically modified host cell of claim 1, wherein the genetically modified host cell is a species of the genus *Escherichia, Enterobacter, Azotobacter, Erwinia, Bacillus, Pseudomonas, Klebsielia, Proteus, Salmonella, Serratia, Shigella, Rhizobia, Vitreoscilla, Paracoccus*, or Clostridia.

12. The genetically modified host cell of claim 11, wherein the genetically modified host cell is a species of the genus *Escherichia*.

13. The genetically modified host cell of claim 1, wherein the genetically modified host cell is a yeast cell.

14. The genetically modified host cell of claim 13, wherein the yeast cell is a species of the *Saccharomyces* genus.

15. The genetically modified host cell of claim 1, wherein the PMD comprises the following amino acid residues: (a) E at position 71, S at position 108, N at position 110, A at position 119, S at position 120, S at position 121, A at position 122, S at position 155, R at position 158, S at position 208, and D at position 302 corresponding to SEQ ID NO:1; or (b) E at position 73, S at position 94, N at position 96, A at position 105, S at position 106, S at position 107, A at position 108, S at position 141, R at position 144, S at position 192, and D at position 283 corresponding to SEQ ID NO:2.

16. The genetically modified host cell of claim 1, wherein the PMD has an amino acid sequence having at least 95% identity with SEQ ID NO:1.

17. The genetically modified host cell of claim 16, wherein the PMD has an amino acid sequence having at least 99% identity with SEQ ID NO:1.

* * * * *